United States Patent [19]

Spears et al.

[11] Patent Number: 5,348,551
[45] Date of Patent: Sep. 20, 1994

[54] METHOD FOR CORRECTING REFRACTIVE DISORDERS

[75] Inventors: Kenneth G. Spears, Skokie; Gerald Horn, Northfield, both of Ill.

[73] Assignee: Kerus Medical Systems, San Bruno, Calif.

[21] Appl. No.: 35,468

[22] Filed: Mar. 23, 1993

Related U.S. Application Data

[63] Continuation-in-part of Ser. No. 512,023, Apr. 16, 1990, Pat. No. 5,263,951, which is a continuation-in-part of Ser. No. 342,202, Apr. 21, 1989, abandoned.

[51] Int. Cl.$^5$ .................................................. A61B 5/06
[52] U.S. Cl. ........................................... 606/5; 606/3; 606/10; 128/898
[58] Field of Search ............... 606/2, 3, 5, 10-19; 128/897, 898

[56] References Cited

U.S. PATENT DOCUMENTS 5,137,530  8/1992  Sand ........................................... 606/5
5,263,951  11/1993  Spears et al. ............................... 606/5

FOREIGN PATENT DOCUMENTS 326760  8/1989  European Pat. Off. ................ 606/4
9012618  11/1990  World Int. Prop. O. ............... 606/5
9201430  2/1992  World Int. Prop. O. ............... 606/5

OTHER PUBLICATIONS

"Ophthalmic Applications of Infrared Lasers-Thermal Considerations" by Mainster; Invest Ophthalmol Visual Sci., vol. 18, NO. 4; Apr. 1979 pp. 414-420.

Primary Examiner—David M. Shay
Attorney, Agent, or Firm—D'Alessandro, Frazzini & Ritchie

[57] ABSTRACT

A method for changing the shape of the cornea of an eye to correct refractive disorders comprises employing laser radiation having a selected wavelength, beam pattern, and beam power profile, and employing this radiation for a selected time duration, wherein the wavelength, beam pattern, beam power profile and time duration are chosen to selectively kill or injure keratocytes and to avoid shrinking the collagen in a selected treatment volume of the cornea which has a posterior boundary which is at least 10% of the total stromal depth, and preferably between 50-90% of the stromal depth.

23 Claims, 7 Drawing Sheets

METHOD FOR CORRECTING REFRACTIVE DISORDERS

RELATED APPLICATIONS

This is a continuation-in-part of co-pending application Ser. No. 7/512,023 filed Apr. 16, 1990 for CORRECTION OF THE OPTICAL FOCUSING SYSTEM OF THE EYE USING LASER THERMAL KERATOPLASTY, now U.S. Pat. No. 5,263,951, which application is, in turn, a continuation-in-part of application Ser. No. 07/342,202 filed Apr. 21, 1989, now abandoned.

BACKGROUND OF THE INVENTION

1. Field of the Invention

The present invention relates to a method and apparatus for changing the shape of the cornea of an eye to correct refractive disorders and, more particularly, to such a method and apparatus which selectively injures or kills keratocytes and avoids shrinking the collagen in the cornea.

2. The Prior Art

Myopia and hyperopia are conditions wherein the light entering a person's eye is not properly focused on the retina. Astigmatism is also the result of improper focus of light onto the retina. Light passes through the cornea of the eye to define an image, and it is now common to attempt to correct for refractive disorders of the type mentioned above by changing the shape of the cornea. Various surgical procedures have been employed, or have been suggested, for this purpose. Most of these procedures involve either mechanical penetration of the cornea or the intentional physical destruction of corneal tissue.

One of these procedures, radial keratotomy, is accomplished by making incisions in a radial pattern around the outer periphery of the cornea; this causes the periphery to bulge slightly and the center of the cornea to flatten. Another of these procedures, lameliar refractive keratoplasty, is accomplished by the placement of material on, or in, the cornea to change its shape. For example, a disk of corneal material from a donor is sutured to the anterior (outer) surface of the cornea, or a synthetic material is implanted within the cornea.

Laser photorefractive keratectomy is accomplished by recontouring the anterior layers of the cornea via ablation of portions of those layers. Intrastromal ablation is accomplished by the use of a laser to vaporize selected areas in the center of the cornea, effectively changing the cornea's shape as the outer portions of the cornea relax into the pockets created by the procedure. Thermal keratoplasty achieves a change in corneal curvature by permanently shrinking collagen fibrils in the cornea. U.S. Pat. No. 4,976,709 to Sand teaches an example of this approach of shrinking collagen fibrils.

The prior art in the area of thermal keratoplasty uniformly teaches achievement of the desired effect by employing treatment techniques which result in collagen shrinkage. Examples of such prior art known to the inventors include U.S. Pat. No. 4,381,007 to Doss; Doss, J. D. and Albillar, J. I., "A Technique for the Selective Heating of Corneal Stroma," Contact Lens, Vol. 6, No. 1, p. 13, Jan.–Mar. 1980; Gasset, A. R. and Kaufman, H. E., "Thermokeratoplasty in the Treatment of Keratoconus," Am. J. Ophthalmol. 79, p. 226 (1975); Doss, J. D., Hutson, R. L., and Albillar, J. I., An Electrothermal Technique for the Alteration of Corneal Curvature," Los Alamos Laboratories Informal Report LA-7155-MS, issued February 1988; Mainster, M. A., "Ophthalmic applications of infrared lasers-thermal considerations," Inv. Ophth. & Vis. Sci., Vol. 18, No. 4, p. 414 April 1979; Rowsey, J. J., Gaylor, J. R., Dahlstrom, R. and Doss, J. D., "Los Alamos Keratoplasty Techniques," Cont. & Intraoc. Lens Med. J., Vol. 6, No. 1, p. 1, Jan–Mar. 1980.

All of the surgical procedures identified above have disadvantages associated with them. Many of these disadvantages result either from a mechanical penetration of the cornea or from a permanent weakening of the structure of the cornea. Any penetration of the cornea includes the risk of infection. Certain procedures, particularly radial keratotomy, also pose the risk of microperforation of the cornea. Corneal inserts introduce the risk of rejection by the cornea. Laser photorefractive keratectomy destroys a portion of a non-regenerative layer of the cornea (Bowman's membrane, which serves as the anchoring membrane for the outermost layer of the cornea), as well as destroying corneal stroma.

Even more disadvantages result from the effects of physical destruction or alteration of corneal tissue. The cornea is uniquely structured to transmit light into the eye. The primary structure of the cornea is the stroma, which comprises approximately 90 percent of the cornea's thickness. The stroma is composed of many relatively long and wide lamellae which run in flat layers from limbus to limbus. The lamellae consist of uniform, parallel, fine collagen fibrils, which are regularly spaced within the lamellae and separated by glycoproteins. It is the thinness of the collagen fibrils and the regularity of their direction and spacing that result in the transparency of the cornea. When this uniformity of size or spacing of the fibrils is disrupted, the proper transmission of light directly into the eye is diminished. It will be appreciated that any surgical procedure leading to a diminishment or disruption of light entering the eye creates an undesirable result. Even when destruction of tissue is avoided, as can be accomplished with laser thermal keratoplasty, the shrinkage of collagen fibrils increases their girth, resulting in an undesirable opacity of the treated area. Current human trials applying this procedure have avoided treatment of the center 3 mm of the cornea, presumably because of the resulting opacity.

BRIEF DESCRIPTION OF THE INVENTION

The present invention relates to a method and apparatus for changing the curvature of the cornea of an eye to correct for refractive disorders. More particularly it is a method and apparatus for changing corneal curvature that uses laser irradiation to activate cellular and biosynthetic processes by selectively injuring or destroying the cells (keratocytes) which exist between the lamellae throughout the cornea, where "selective" means that the injury or damage is preferential to keratocytes and does not result in shrinkage or destruction of the pre-existing collagen within the treatment volume.

The present invention uses irradiation to create a unique effect in the treated volume of the corneal stroma, one characterized by the structural integrity of the irradiated stroma, with no destruction or shrinkage of the pre-existing collagen which are characteristic of prior-art processes, but with a distributed, selective decrease in the pre-existing keratocyte population. This effect is neither taught nor suggested by the prior art. The intentional triggering of a desired biological response to the cellular injury or death, in a pattern distributed adjacent to and throughout the treated volume of the stroma is unique to the present invention. This biological response, which includes the process of keratocyte reproduction, migration, and repopulation, results in an addition of new collagen and other compounds to the pre-existing stromal architecture over time. As a result of the biological response, the stroma develops different mechanical properties that alter the corneal curvature in a particular manner.

The treatment employed by the present invention requires, within the treatment volume, a certain degree of keratocyte injury. A parameter $\Omega$ defines keratocyte injury. An $\Omega$ of 0.5 is the threshold for significant cell injury. This parameter $\Omega$ must be $>0.5$ at some significant corneal depth and volume for treatment to be effective according to the present invention. There is also an upper limit on the treatment taught by the present invention which is to avoid shrinkage of collagen. This limit is based on the temperature generated in the cornea during treatment.

Because the cornea has a delicate layer of endothelial cells at its most posterior layer, the present invention teaches an additional restriction on the extent of cell injury in this layer; the preferred embodiment has a posterior boundary (where posterior boundary is defined as those points in the posterior portion of the treated volume of the cornea beyond which $\Omega<0.5$) that is less than the full corneal thickness, and requires that, at the endothelial layer, cell death be minimal (recognizing that 3–10% of cell loss in the endothelium may be clinically acceptable in less preferred treatments). The least amount of useful keratocyte cell injury is believed to require a posterior $\Omega$ boundary at about 10% of the stromal depth and a minimum depth of about 50% is presently preferred. For effective treatment near this limit, retreatment after several weeks may be needed, and/or multiple treatments per session may be needed to achieve significant effects.

According to the present invention, the laser treatment parameters are selected to meet the following relationship: $\Omega \geq 0.5$ at significant depth in the corneal stroma; where the preferred range of the posterior boundary is 50–90% of the total stromal depth (although it is believed that depths of as little as 10% may be effective) and where the laser power needed to achieve a specific depth is dependent on the laser wavelength, beam pattern (the shape of the laser radiation projected onto the cornea), beam profile (the power density within the beam pattern), and time; where the pulse duration is $\geq 1.5$–15 sec. The specific minimum pulse duration depends on the wavelength selected, such that larger water absorption coefficients, such as 114 cm$^{-1}$, require longer times. Once the laser wavelength and beam pattern are selected, and the posterior boundary is constrained to be $<90\%$ of the stromal depth, then the upper value for laser power is constrained by the beam profile and pulse duration. These conditions will avoid collagen shrinkage.

A computer model of laser thermal effects in the cornea has been developed to aid in the selection of treatment parameters to accomplish the goals of the present invention. The model embodies the empirical results of histopathologic studies and incorporates predictive equations for cell death, and is therefore usefully employed in practicing the present invention for predicting specific depths and areas of cell damage as a function of treatment parameters. The model includes the effects of evaporation and could be easily supplemented to account for any additional cooling by liquid or vapor on the surface of the cornea. A presently preferred computer model is included in Appendix I to this specification.

The present invention describes a form of corneal stromal treatment in which the cellular and biosynthetic processes are essentially additive to the pre-existing corneal structure. The treatment creates preferential injury within the treated area to the diffusely spread keratocytes, which is followed by cellular response and biochemical synthetic processes. Though the exact cause is unknown, the effect is believed to cause resistance to the internal eye pressure and thereby flatten or reduce the curvature of the cornea in the treated area. The effect of new keratocyte repopulation and accompanying collagen synthesis might increase tensile strength of the cornea and "stiffen" it by decreasing the bending moment. Also, newly synthesized collagen diffusely spread throughout the treated area may provide contractive forces due to formation processes. Additional contractive forces may occur as a result of keratocyte formation, migration and repopulation. It is also possible that the selective injury to the keratocytes results in a change in the glycoprotein matrix surrounding the collagen fibrils. The refractive effect has been seen to occur in rabbits over a time course of days to about 8 weeks.

As previously noted herein, it has been recognized that laser radiation can be delivered to the eye to effect direct physical changes in different regions and in different tissues, and also in a selective manner so that adjacent tissue is not affected. However, it has never been recognized or anticipated that laser radiation can be efficaciously employed to selectively injure or destroy cells in a tissue without destroying during the procedure the pre-existing extracellular material, such as collagen, of the treated tissue. Nor has it been recognized or anticipated that laser radiation can be employed to selectively activate a desired biological response through the selective injury or destruction of only the cells in the treated tissue. Nor has it been recognized or anticipated that laser radiation can be employed to selectively activate such a desired biological response which leads to a change in the curvature of the treated portion of a cornea without destroying or shrinking collagen during the procedure.

DETAILED DESCRIPTION OF A PREFERRED EMBODIMENT

Those of ordinary skill in the art will realize that the following description of the present invention is illustrative only and not in any way limiting. Other embodiments of the invention will readily suggest themselves to such skilled persons.

Figure 1:
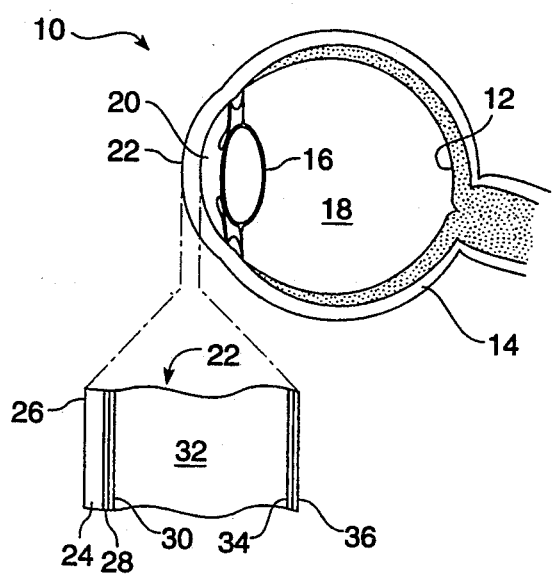
FIG. 1 is a view in cross section of the human eye, with a magnified cross section of a portion of the cornea.

A general description of an eye will aid in understanding the invention. Referring particularly to FIG. 1, the human eye 10 is a system of lenses which focus light on a retina 12 located to the rear of a substantially spherical body defined by a sclera 14. These include a lens 16 which separates the vitreous body 18 from an anterior chamber 20, and the cornea 22 which defines the forward wall of the anterior chamber 20 and which also acts as a lens. The cornea 22 is a smoothly curved, clear structure which has a smaller radius of curvature than the opaque sclera 14 and which bulges slightly from the smooth outer contour of the eye.

Refractive errors occur when these lenses do not focus the incoming light on the retina 12. In such case, additional corrective lenses such as glasses or contact lenses may be added to provide clear vision. In the alternative, the corneal curvature of the eye may be changed to make the proper correction in focal power. Such changes in focal power are measured in increments called diopters.

The present invention relates to changing the focal power of the eye lenses by altering the shape, or curvature, of the cornea 22. Referring still to FIG. 1, the cornea 22 comprises a number of distinct layers of tissue which together have a thickness ranging from 490 to 650 microns at the center and 600 to 1,000 microns at the periphery. These include an epithelium 24 which presents a very smooth and clear outer surface 26 exposed to the surrounding environment. It has a thickness of about 50 microns. Immediately behind the epithelium 24 are two very thin layers, a basal membrane 28 and Bowman's membrane 30 which together typically are from 10 to 17 microns thick. Many documented complications can be avoided by not disturbing these two membranes below the epithelium 24 when implementing any corrective strategy. When these membranes remain, any epithelium that is necrotized is easily and quickly regenerated.

The main body of the cornea is composed of a thick layer called the corneal stroma 32 which comprises up to 90% of the cornea's thickness. The corneal stroma 32 comprises cells called keratocytes dispersed between the numerous wide, thin layers called lamellae containing collagen fibers surrounded by a glycoprotein matrix. For the purpose of the present invention, it is important to note that 78% of the corneal stroma is composed of water.

Located behind the corneal stroma are two thin layers, Descemet's membrane 34 and the endothelium 36. Descemet's membrane 34 has a thickness of about 7 microns and the endothelium 36 is a single layer of cells having a thickness of about 5 microns.

The cornea 22 is the eye's greatest refracting lens. Several conditions, including myopia, hyperopia, and astigmatism, result from improper image formation on the retina 12, and while these conditions may not be caused by the cornea 22, all three can be corrected by reshaping the cornea 22.

The instant invention is a method of changing the shape of the cornea 22 without causing shrinkage of the pre-existing collagen at the cornea treatment site. While the method is similar to laser thermal keratoplasty in the sense that laser energy is used, unlike the methods taught by the prior art, care is taken to assure that the heating effect of the radiation does not result in collagen shrinkage.

The present invention uses irradiation to create a unique effect in the treated volume of the corneal stroma 32, one characterized by structural integrity of the irradiated stroma, with no destruction or shrinkage of the pre-existing collagen, but with a distributed, selective decrease in the pre-existing keratocyte population. This biological response, which includes the process of keratocyte reproduction, migration, and repopulation, results in an addition of new collagen and other compounds to the pre-existing stromal architecture over time. As a result of the biological response, the stroma develops different mechanical properties that alter the corneal curvature in a particular manner.

The cornea 22 has collagen throughout the stroma 32 and in the important membranes on both sides of the stroma 32. The stromal architecture is unusual in that over its nominal 0.5 mm of thickness the collagen is arranged in sufficient order to provide little light scattering (i.e., corneal clarity) while providing strength to resist the internal eye pressure. Collagen is a triple helix of three proteins of 300 nm length, where the types of amino acids in the proteins define the type of collagen (e.g., Type I is the main structural collagen in the cornea). The collagen molecule is organized into small bundles of about 5 molecules called microfibrils, where collagen molecules stack with offsets of about $\frac{1}{4}$ their molecular length. These microfibrils further stack into larger diameter and longer structural units called fibrils. Naturally occurring crosslinks both between the three proteins in the triple helix and between collagen molecules in microfibrils add extra stability to mechanical stress and heat effects.

In the corneal stroma 32 the fibrils exist in layers (lamellae) of aligned fibrils where each fibril is only about 25–35 nm in diameter and the lamellae have lengths of macroscopic corneal dimension (about 10 mm). The fibrils in corneal stroma are surrounded by other bio-molecules such as polysaccharides and glycoproteins, that provide a spacing between fibrils in each layer. The small diameter of stromal fibrils is important in achieving the necessary ordering that provides corneal clarity. The stroma has small, well ordered and separated collagen fibrils, while the white of the eye, the sclera, has a wide range of fibril diameters, from about 25–230 nm, in entangled bundles, which scatters light and produces the characteristic white color of the sclera.

In literature addressing collagen heating experiments, the state of partial denaturation of collagen tissue was often called shrinkage, with extreme denaturation often called coagulation. "Collagen shrinkage" is essentially an operational statement that heating proceeded to a point where subsequent cooling of the collagen tissue left the tissue at reduced length; in this literature, shrinkage has been used to describe a permanent change in collagen tissue dimensions. When applied to corneal collagen, the thermodynamics involved indicate that the change will have occurred upon completion of the heating and cooling cycle, and that it is permanent even after a long delay.

The presence of collagen shrinkage can be detected by optical microscopy in polarized light ("birefringence" studies). Birefringence studies on animal corneas treated by the method taught in the present invention demonstrated no shrinkage of collagen. Following such treatments by the inventors, some animals were sacrificed at 2 hours and some at 3 days post-treatment; thin corneal cross-sections from these animals were then studied. These microscopic studies using polarized light indicated normal collagen structure in the treated corneas; that is, no collagen shrinkage had occurred.

The preferred embodiment of the present invention requires, within the treatment volume, a parameter defining keratocyte injury, $\Omega$, that is $\geq 0.5$ at some significant corneal depth and volume for effectiveness. To avoid overcomplicating the disclosure, an explanation of the derivation and use of $\Omega$ in connection with the present invention is provided in Appendix I hereto.

An $\Omega$ of 0.5 is the threshold for significant cell injury. Because the cornea has a delicate layer of endothelial cells at its most posterior layer, the specific embodiment includes a restriction on the extent of cell injury in this layer; the preferred embodiment has a posterior boundary (where posterior boundary is defined as those points in the posterior portion of the treated volume of the cornea beyond which $\Omega < 0.5$) that is less than full corneal thickness, and requires that, at the endothelium layer, cell death be minimal (recognizing that 3-10% of cell loss in the endothelium may be clinically acceptable in less preferred treatments). It is believed that the least amount of useful keratocyte cell injury requires a posterior $\Omega$ boundary of about 10% of the stromal depth but depths of between about 50% and 90% are preferred. For effective treatment near this limit, retreatment after several weeks may be needed, and/or multiple treatments per session may be needed to achieve significant effects. Such multiple treatments may occur at intervals of between 10 seconds and one hour between treatments. There is also a limit on the treatment taught by the present invention which is to avoid the shrinkage of collagen. This limit is based on the temperature generated in the cornea during treatment.

The laser treatment parameters are selected to meet the following relationship: $\Omega \geq 0.5$ at significant depth in the corneal stroma; where the preferred range of the posterior boundary is 50-90% of the total stromal depth and where the laser power needed to achieve a specific depth is dependent on the laser wavelength, beam pattern (the shape of the laser radiation projected onto the cornea), beam profile (the power density within the beam pattern), and time; and where the pulse duration is $\geq 1.5$-15 sec. The specific minimum pulse duration depends on the wavelength selected such that larger water absorption coefficients, such as $114 \text{ cm}^{-1}$, require longer times. Once the laser wavelength and beam pattern are selected, and the posterior boundary is constrained to be $<90\%$ of the stromal depth, then the upper value for laser power is constrained by the beam profile and pulse duration according to the computer model in Appendix I.

The damage parameter $\Omega$ and related parameters discussed in Appendix I were not known for cellular constituents of cornea prior to the present work, and the derived parameters have had useful interpolation and prediction properties for new experimental conditions near the parameter ranges utilized in this invention. The assessment of damage levels in skin through histologic studies, and the correlation of the studies to some specific value of $\Omega$, has been documented in the literature. For the cornea, histologic studies of treatments using the invention demonstrate that there are very sharp spatial boundaries within which keratocyte necrosis is essentially complete. The region of complete necrosis is where $\Omega \geq 1$ and a value of 0.9 or 1.0 may be taken as the boundary of complete necrosis. An $\Omega = 0.5$ has been empirically determined to represent the point of significant, irreversible cellular damage. Although the mathematical function for $\Omega$ is continuous, and smaller values of $\Omega$ might indicate a smaller fractional damage level, for cells there is probably a value of $\Omega$ below which no effective damage occurs. The value of $\Omega = 0.1$ has been used in the present modeling to be a point with essentially no damage, but it is probable that only nominal damage takes place up to values of 0.2-0.3.

A computer model of laser heating in the cornea that includes predictive equations for cell death based on histologic study is useful for predicting specific depths and points of cell damage as a function of treatment parameters. An illustrative example of such a computer model is included in Appendix I. This model can calculate the effects of evaporation and also could be easily supplemented to account for any additional cooling by liquid or vapor on the surface of the cornea. Examples of treatments given herein are only for corneas that received no additional cooling. However, treatments including additional cooling can easily be derived from the model by those skilled in the art.

The computational model for predicting temperature-time profiles and cell damage parameters, included in Appendix I, assumes a corneal absorption coefficient equivalent to water for purposes of radiation absorption and, for purposes of thermal diffusion, it assumes a specific percentage of the cornea is water. A model having specific layer properties of absorption and thermal diffusion could be developed, but the basic damage predictions in the stroma are not critically dependent on such refinements. For convenience in representing laser absorption properties that include the epithelium, stroma, endothelium and vitreous humor, 100% water content has been selected, which is close for all but the stroma which has a 78% water content. Tests indicate that the histological observations can be accounted for over a range of parameters with this model. The utility of the cell damage model and temperature-time model is in predicting the effects of treatment combinations of laser wavelength, beam pattern, beam profile, and pulse duration within the overall ranges of the present invention.

It is significant to note that the changes in corneal curvature which result from the present invention occur over time and are not fully realized immediately posttreatment. This is consistent with a process which results not from collagen shrinkage but from a biological response to the destruction of keratocytes. The fact that cells are damaged by heating with no damage to collagen should not be surprising, since collagen is a relatively stable biological protein molecule due to its triple helix structure. In contrast, living cells have many constituents, such as enzymes, that can be affected by heat, as well as the membrane wall itself, which is rather sensitive to thermal disruption. Experiments performed by the inventors have employed histopathology to assess cellular damage, and these studies confirm that endothelial cell and keratocyte necrosis occur at similar time-temperature profiles. Collagen studies by the birefringence method show that higher temperatures are required to cause shrinkage.

Studies by the inventors demonstrate that the treatment parameters taught herein create preferential effect within the treated area to the diffusely spread keratocytes and do not shrink the lamellary collagen. This unique and selective effect allows cellular and biosynthetic processes to subsequently occur that are essentially additive to the pre-existing structure of the cornea.

The embodiment of the method described above is preferably implemented by using a laser which has an appropriate absorbing wavelength. As a very general proposition, laser energy produced by lasers with very short wavelengths (for example, argon ion lasers at 0.4880 microns, or Nd:YAG lasers at 1.06 microns) is not absorbed sufficiently by the cornea 22 and passes through the cornea 22 to be absorbed by other structures in the eye. On the other hand, laser energy produced by lasers with very long wavelengths (for example, $CO_2$ at 10.6 microns, HF at 2.9 microns, or Erbium at 2.83 microns) is highly absorbed by the outer layers of the cornea 22 and does not reach the corneal stroma 32 without overheating the outer layers 24, 28 or 30.

Figure 2:
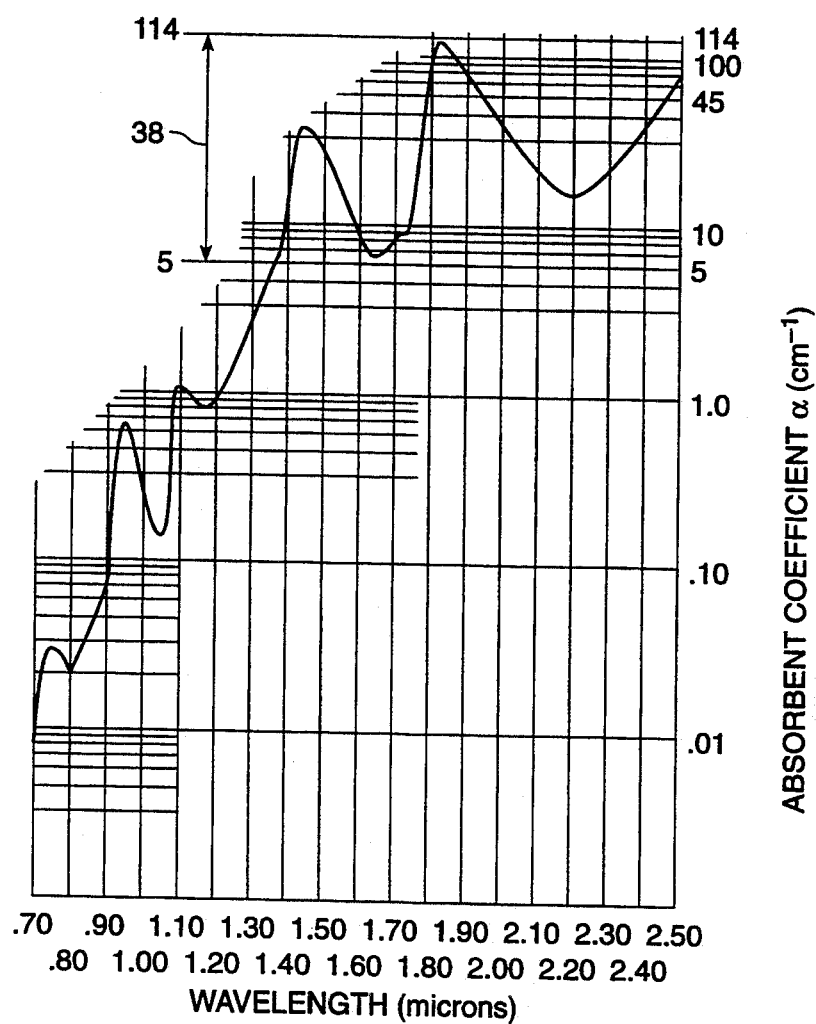
FIG. 2 is a graphic representation of the absorption characteristics of water.

As illustrated by the absorption graph of FIG. 2, the relationship between laser wavelength and depth of absorption is far from linear. Such graph is a plot of the absorption coefficient of water as a function of laser wavelength in microns. It is readily apparent that although the general rule holds true that increased wavelength results in greater absorption, within selected ranges of the entire spectrum the curve is very nonlinear and is even contrary to the general rule. It is a teaching of the present invention that an important factor in obtaining proper laser treatment of the corneal stroma is the selection of a wavelength for the laser which provides the desired absorption.

Absorption coefficients as referred to herein are defined in terms of the exponential attenuation of the incident intensity of the laser beam and are expressed in $cm^{-1}$. More specifically, absorption coefficients ($\alpha$) for water which are within the range of 5 $cm^{-1}$ to 114 $cm^{-1}$ are believed to be usable for proper treatment of the corneal stroma in accordance with the invention. This usable range of absorption coefficients is indicated by the double-headed arrow 38 in FIG. 2. Furthermore, it is believed that the control of the procedure is best in a range of about 20 $cm^{-1}$ to 80 $cm^{-1}$. As the absorption curve in FIG. 2 indicates, laser wavelengths of 1.38 microns to 2.50 microns (and up to 2.70 microns, by extrapolation of the illustrated curve in FIG. 2) have absorption coefficients that are included within the usable range.

Figure 3:
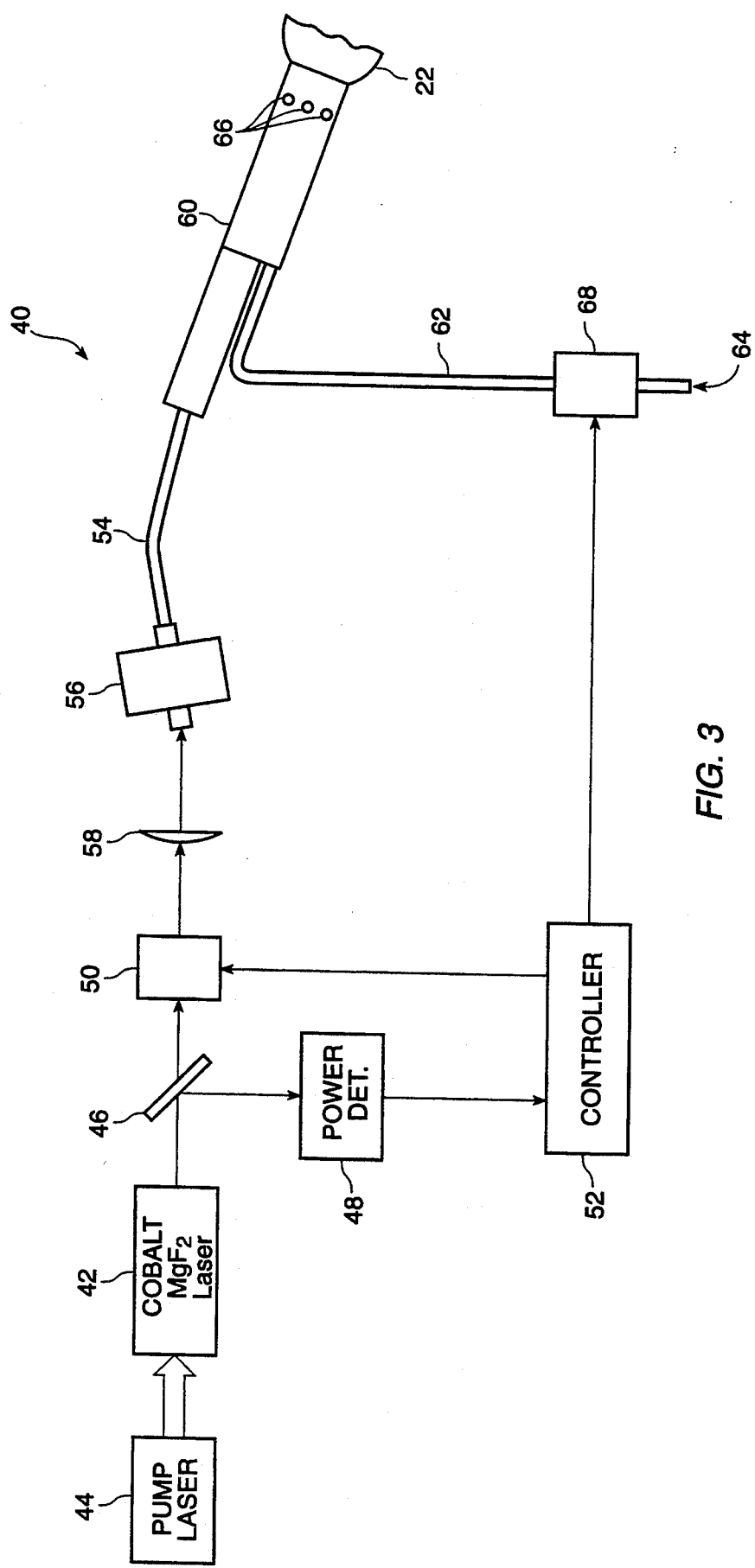
FIG. 3 is a pictorial representation of an illustrative laser treatment system for practice of a preferred embodiment of the method of the present invention.

Referring particularly to FIG. 3, an illustrative laser system 40 for practicing the method of the invention includes a number of elements. The heart of the system is a laser 42 which is preferably a $Co:Mg:F_2$ laser, broadly tunable to a wavelength within the range of 1.55 microns to 2.25 microns. The laser 42 is pumped by a continuous wave, 1.32 micron Nd:YAG laser 44, and it produces a continuous average output of from 0.5 to 2.0 watts at the indicated range of wavelengths. Construction of the preferred laser 42 is described in an article by Peter F. Moulton "An Investigation of the $Co:Mg:F_2$ Laser System", in IEEE Journal of Quantum Electronics, Vol. QE-21, No. 10, October 1985.

The output of the laser 42 is directed to a beam splitter 46 which directs a fixed proportion of its energy to a power detector 48 and allows the remainder of the energy to pass through to an electronically operable shutter 50. Power detector 48 provides a signal which indicates the level of the laser energy delivered to the shutter 50 and this power signal is input to a controller 52. The electronic shutter 50 is controlled by an output on the controller 52 to interrupt the laser beam and thereby control the pulse duration, pulse rate, and duty cycle of the delivered laser energy. Alternatively, the power to the laser 42 could be used to provide control of the pulse duration.

The controlled laser energy is delivered to the cornea 22 by an optical fiber 54. The input end of the optical fiber 54 extends through a tiltable mount 56, and the laser energy is focused on this end by a convex lens 58. The tiltable mount 56 holds the end of the optical fiber 54 to be tilted with respect to the longitudinal axis of the laser beam emanating from the lens 58. As will be explained below, the adjustment of this tilt angle enables the energy density of the laser beam to be contoured such that less energy is delivered at its center than its periphery. This adjustment and the distance between mount 56 and lens 58 can be used to adjust the degree of radial uniformity in different parts of the beam.

The other end of the optical fiber 54 connects to a probe assembly 60 which engages the cornea 22 and is held in fixed relation thereto. The probe assembly 60 has a number of configurations which will be described in more detail below, but preferably it also includes connections to a hose 62, which delivers a stream of cooling gas, such as Freon, which is input at 64 and flows into the probe assembly 60 where it cools the surface of the cornea 22 being treated. The cooling gas exits through openings 66 around the periphery of the probe assembly 60, and the flow of cooling gas is controlled by an electric gas valve 68 which connects to an output on the controller 52.

Figure 4:
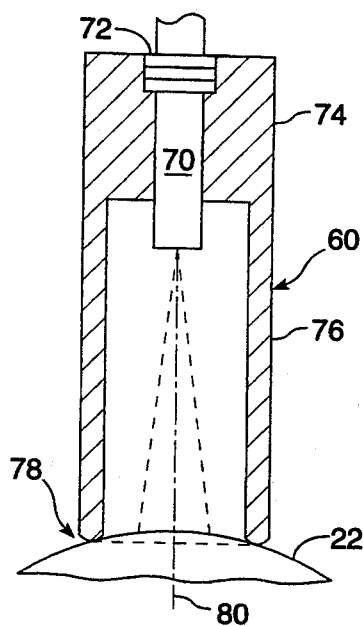
FIG. 4 is a view in cross section of a probe assembly which may be employed as a part of the system of FIG. 3.
Figure 6A:
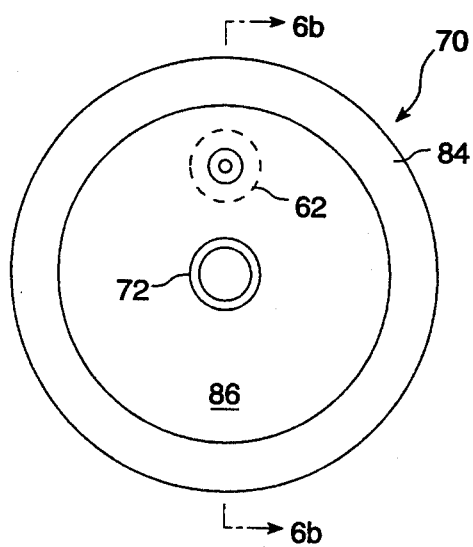
FIGS. 6A and 6B are views in cross section of the probe which forms part of the assemblies of FIGS. 4 and 5.
Figure 6B:
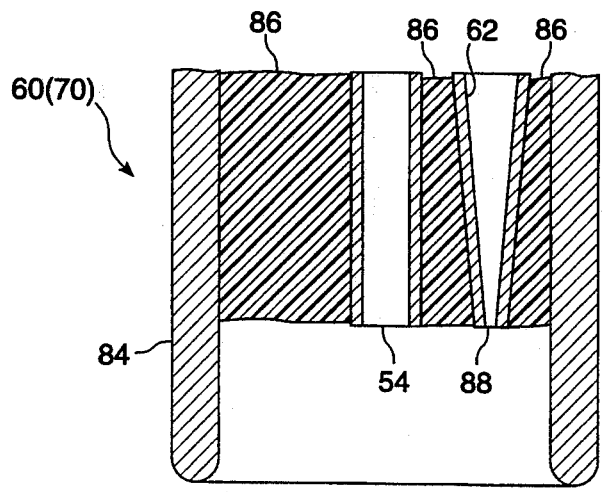

Referring to FIG. 4 and to FIGS. 6A and 6B, a first embodiment of the probe assembly 60 includes a circular cylindrical metal probe 70 which connects to optical fiber 54 and the hose 62 (FIG. 3). A threaded flange 72 is machined around the probe 70 and it is received in a threaded opening formed on the enclosed end 74 of a circular cylindrical metal collar 76. The collar 76 presents an annular shaped forward end 78 that is smoothly rounded and suitable for engaging the surface of a cornea 22. The probe assembly 60 is retained in engagement with the cornea 22 by hand pressure, the technique commonly employed when using contact lenses in eye surgery. Using this technique, the probe assembly 60 remains aligned with the optical axis 80 of the eye despite small eye movements by the patient.

The laser energy is directed out the forward end 78 of the probe 70 and is coaxial with the optical axis of the eye 80. The laser energy is distributed in a substantially circular pattern and it diverges slightly as it travels away from the end of the probe 70. Indeed, the size of the circular laser pattern which impinges on the cornea 22 is determined by selecting a collar 76 of the appropriate length. That is, a set of collars 76 of varying lengths are provided and may be easily attached to the threaded probe 70. Each collar 76 provides a circular treatment pattern of calibrated size.

Figure 5:
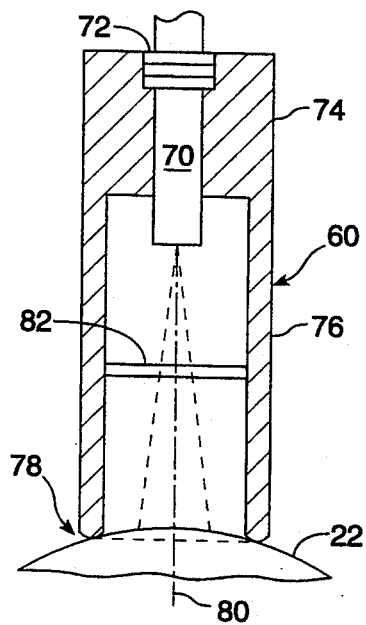
FIG. 5 is a view in cross section of an alternative probe assembly which can be used in the system of FIG. 3.

A second embodiment of the probe assembly 60 is illustrated in FIG. 5. A filter 82 is added to probe assembly 60 to create a specific pattern from the beam. Filter 82 comprises an optically opaque disk having a centrally located optically transmissive treatment pattern formed therein.

The construction of the probes 60 and 70 is shown in detail in top and cross sectional views in FIGS. 6A and 6B, respectively. Probes 60 and 70 comprise a metal sleeve 84 which receives the optical fiber 54 and the hose 62. These elements are fixed in the positions shown with an epoxy binder 86 which fills the voids and extends downward substantially level with the exposed ends of the optical fiber 54 and the hose 62. As shown best in FIG. 6B, the end of the hose 62 is constricted to form a nozzle 88 that causes a pressure drop in the Freon gas exiting therefrom. As is well understood by those of ordinary skill in the art, this pressure drop lowers the temperature of the cooling gas.

It will be recognized that the above arrangement provides the control for carrying out the method of the invention. It should be apparent that many alternative structures may be employed. For example, lasers which will produce the appropriate treatment wavelengths to provide the required absorption coefficients in water of between 5 $cm^{-1}$ and 114 $cm^{-1}$ are in the range of about 1.38 microns to about 2.70 microns and can be constructed using Holmium$^{+3}$ ions, Thulium$^{+3}$ ions or Erbium$^{+3}$ ions or mixtures thereof, in either a YAG, YSGG, YLF, or YVO$_4$ crystalline media. The laser 42 may also be a diode laser constructed to produce energy of the proper wavelength. Also, the laser 42 may be pumped by a diode laser of the proper wavelength as described in an article by Thomas M. Baer "Diode Laser Pumping of Solid-State Lasers" published in the June 1986 issue of *Laser Focus*.

The selected treatment volume most desirably damages less than 10% of the endothelial cells of the cornea. The particular treatment parameters used will depend on the type of correction to be made and the degree of correction (diopters) desired. For example, three illustrative treatment patterns are shown which may be employed for treatments according to the present invention.

Figure 7:
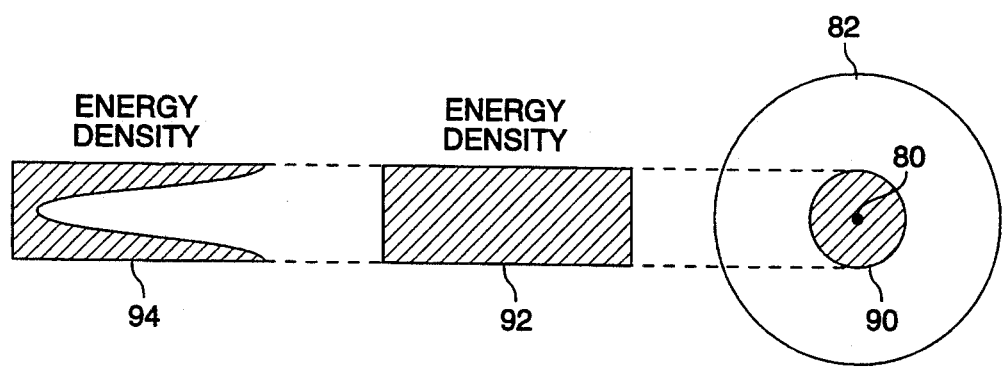
FIGS. 7-9 are pictorial views of treatment patterns for correction of myopia using the system of FIG. 3.

First, a filter 82 employing a treatment aperture in the shape of a central disc as shown in FIG. 7, may be employed to correct myopia. FIG. 7 shows the energy profile across a treatment disk 90 shown centered along the optical axis 80 of the eye. While the beam profile (power density) across the treatment disc 90 may be uniform as shown graphically at reference numeral 92, the preferred approach is to contour the energy density profile as shown at reference numeral 94 such that it is reduced near the optical axis 80 of the eye. This is accomplished, for example, by tilting the input of the optical fiber with respect to the applied laser beam as described above. The greater the tilt, the lower the power density at the center of the output beam. Alternatively, the beam profile can be filtered by absorbing or reflecting elements with standard techniques known to those skilled in the laser arts.

Figure 8:
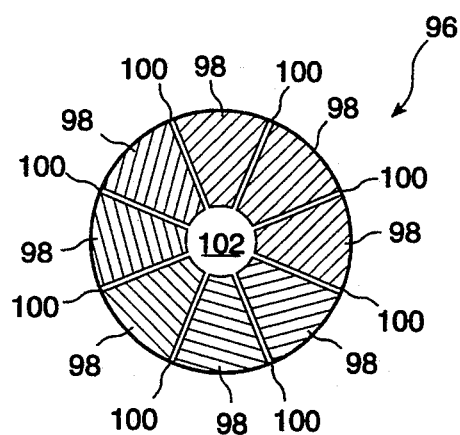

To correct for hyperopia, a steepening of the central corneal surface is required. This can be accomplished by strengthening or "tightening" the area around the central cornea, causing it to bulge in response. A filter 96 employing one or more apertures in the form of radial sectors is capable of treating both myopia and hyperopia and is shown in FIG. 8. The filter 96 in the embodiment of FIG. 8 is shown employing eight equally spaced radial sectors 98, although other numbers of sectors and other spacings may be employed to treat specific conditions. The shaded areas define optically clear portions of the filter representing treated areas and the clear areas define opaque portions of the filter representing untreated areas. The preferred treatment for myopia will include treatment regions within the approximately 5 mm diameter region around the optical axis 80 of the cornea, while the preferred hyperopia treatments will be made in the region outside of the 5 mm diameter circle.

As presently preferred, the treatment sectors 98 are produced using filters designed to provide symmetrical patterns having 3, 4, 6, 8, 10, and 12 sectors. Alternatively, one or more sectors could be applied at different positions in successive treatments to make a complete pattern. The opaque radial regions 100 may have a length from 1 millimeters to 6 mm. The diameter of the untreated central region 102 of the cornea ranges from zero to 4.0 mm, depending on whether treatment of myopia or hyperopia is desired, and the width of each treatment sector 98 leaves gaps between sectors 98 from 0.25 to 1.5 mm.

Figure 9:
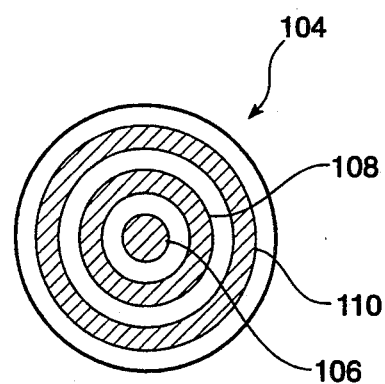

Finally, a filter 104, for the treatment of myopia, employing a number of concentric annuli disposed about a central disk is depicted in FIG. 9. As in FIG. 8, the shaded areas represent clear portions of the filter defining treated areas and the clear areas represent opaque portions of the filter representing untreated areas. The central disc pattern 106 is coaxial with the optical axis 80 of the eye and it may have a radius from zero to 3 mm, although a range of 1 to 2.5 mm is preferred. FIG. 8 shows two concentric annuli 108 and 110 disposed about the central disk pattern 106. The radius of the central disk pattern 106 may range from about zero to 3 mm in diameter; the treatment annuli may range from about 0.25 to 2 mm in radial width, and the resultant untreated annuli may range from about 0.25 to 2 mm in radial width.

Many treatment patterns may be used to correct for astigmatism. The above described patterns for myopia and hyperopia perform their corrective functions by altering the corneal curvature about the central optic axis. This is achieved by using treatment patterns which are symmetrical about the central optic axis in more than two directions. In contrast to such treatment patterns having 3 fold or greater rotational symmetry, astigmatic corrections can be made with treatment patterns which have no more than "2 fold symmetry".

Figure 10:
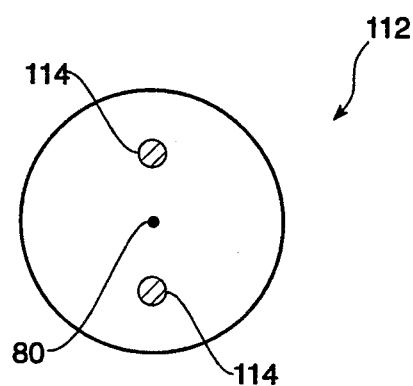
FIGS. 10 and 11 are pictorial views of alternative treatment patterns for correction of astigmatism.
Figure 11:
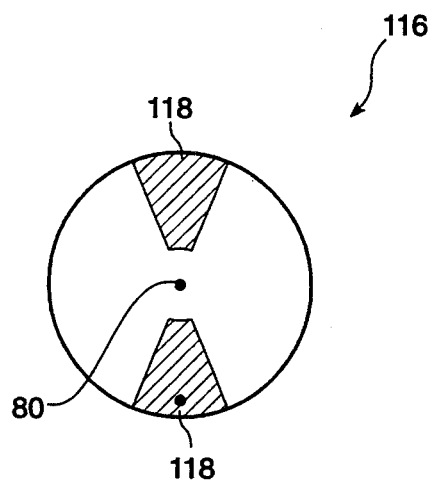

Two such patterns are shown in FIGS. 10 and 11 where the treatment zones are located symmetrically above and below the central optic axis 80, but none are located symmetrically to the left and right as in the pattern of FIG. 8. Such 2 fold symmetric treatment for astigmatism is shown in filter 112 of FIG. 10 as circular patterns 114, and in filter 116 of FIG. 11 as sector patterns 118. In addition, it may be possible to correct astigmatism with only single treatment sectors. Conceivably, such sectors where only flattening is desired could be diagnosed through the use of corneal topography systems and the shape of the treated sectors might be custom designed for certain patients. The treatment parameters for the astigmatic patterns are similar to those discussed above.

Those of ordinary skill in the art will recognize that the disk patterns depicted herein are meant to be illustrative only and that other patterns may be found to be useful in treating certain conditions. The present invention is, therefore, not to be limited by these disclosed patterns.

Table A contains the result of sample treatment parameters which were applied to rabbit eyes with a central disc pattern having a contoured profile similar to that graphically shown at 104 in FIG. 7. To achieve this beam profile, a cylindrically symmetric absorbing filter was employed. The beam profile has a relative power level as a function of radial distance which is measured by scanning the laser beam with a small aperture at the entrance of a power meter. Additional power measurements were taken through a much larger hole of nearly a millimeter in order to provide a measure of peak power over a size that is more significant for laser treating effects on corneal structures.

The laser profile (power density) measured relative to radial positions on the cornea was 50% of the peak power at a 2 mm radius, 90% at a 1.6 mm radius, maximum power at a 1.1 mm radius, and had a central area of reduced power. The central area, when measured through an aperture of 0.042 inch diameter (1.067 mm), was 45% of the maximum power, when measured with the same aperture centered at a 1.1 mm radius. The resulting contoured pattern produced curvature changes in the cornea for the central 2.5-3 mm diameter resulting in the corrections reported in Table A. By increasing the distance from the fiber to the cornea this pattern can be applied over larger areas.

TABLE A

Myopic Corrections Using a Contoured Central Disc Pattern

| Average Joules/mm$^2$ | Maximum Watts/mm$^2$ | Time (Seconds) | Wavelength (microns) | Correction (Diopters) |
|---|---|---|---|---|
| 0.16 | 0.053 | 4 | 2.06 | 4.7 |
| 0.20 | 0.033 | 8 | 2.06 | 5.5 |
| 0.22 | 0.036 | 8 | 2.00 | 1.8 |
| 0.21* | 0.034 | 8 | 2.00 | 4.7 |
| 0.20 | 0.033 | 8 | 1.97 | 1.4 |
| 0.20 | 0.033 | 8 | 1.94 | 0.8 |

*Denotes two successive treatments with a nominal delay of about 20 seconds.

In regard to Table A it should be noted that the duty cycle for the laser used was 100% (i.e., a continuous laser). The average Joules/mm$^2$ is measured using a 1.067 mm diameter aperture at a radius of 1.1 mm. The curvature correction measurements reflect an average over the center 3 mm diameter; the measurements in Table A are for various post-treatment intervals, although all intervals are at least as long as 172 days for identifying the correction.

The data in Table A identifies a range of wavelengths which were experimentally used in rabbit eyes and produced results which are believed to be useful. As depicted in FIG. 2, these wavelengths correlate to absorption coefficients in the range of about 38 cm$^{-1}$ to 114 cm$^{-1}$. In addition, the tabulated data suggests the possible effectiveness of employing multiple treatments to achieve corneal correction.

Figure 12:
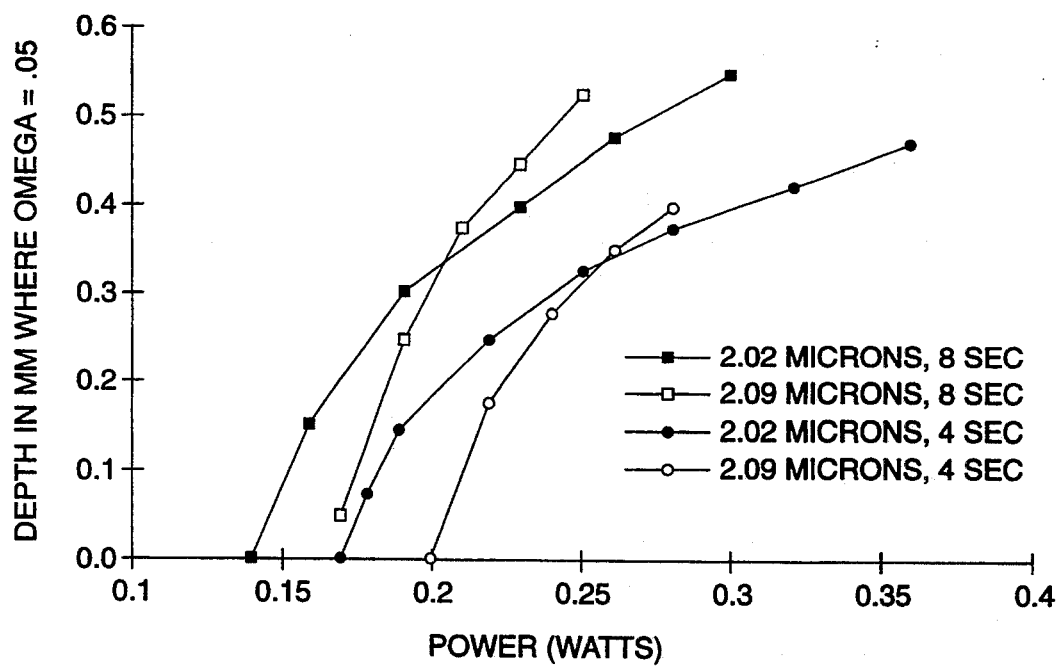
FIGS. 12 and 13 are graphs presenting illustrative examples of the relationships between treatment parameters according to the present invention.
Figure 13:
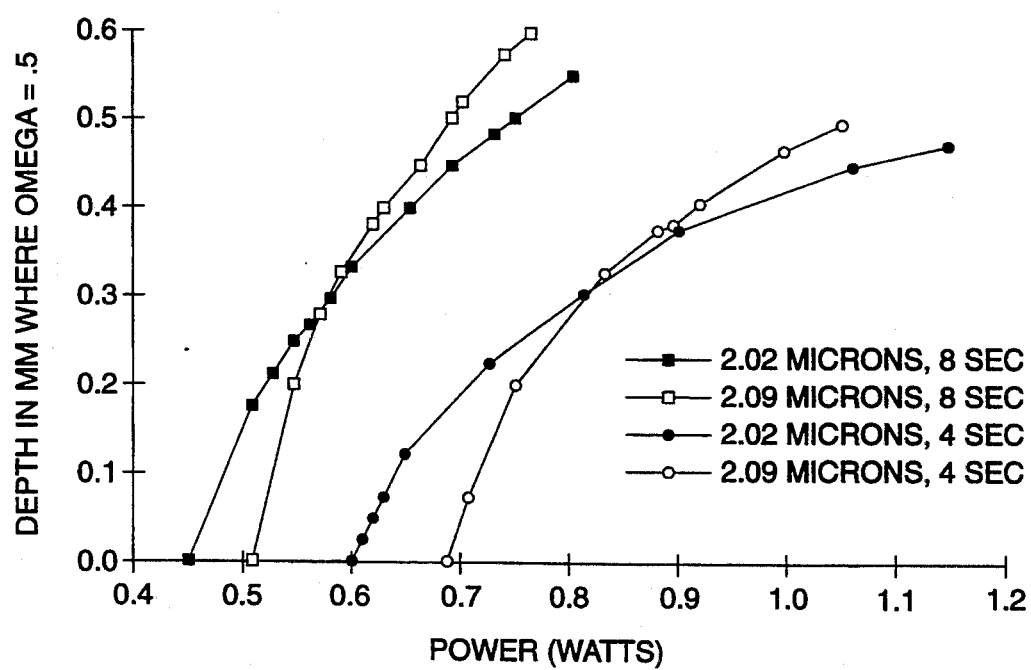

To further aid in an understanding of the present invention, FIGS. 12 and 13 present specific illustrative examples of the relationships between treatment parameters. Those of ordinary skill in the art will recognize that the illustrative specific examples set forth in FIGS. 12 and 13 do not represent the only possible parameters which fall within the teachings of the present invention. An exhaustive catalog of all permutations of such parameters would unduly complicate the disclosure herein. The computer model of Appendix I may be used to generate other sets of treatment parameters within the scope of the present invention.

FIGS. 12 and 13 are illustrative of the relationship between certain treatment parameters where, for FIG. 12, a 2 mm circular pattern with a flat beam profile (i.e., a constant power density across the pattern) is employed, and, for FIG. 13, a 4 mm circular pattern with a flat beam profile is employed. In the flat beam profile used in the 4 mm example of FIG. 13, about 77% of the total energy was contained in a uniformenergy central section of the beam profile having a power density of 0.0613 W/mm$^2$ (at 1 watt total energy). The rest of the energy was in sloped edges of the beam profile as will be appreciated by those of ordinary skill in the art. In both FIGS. 12 and 13 the relationship between the necessary laser power and the depth of the desired posterior treatment boundary (the depth beyond which $\Omega$ is less than 0.5) is plotted for two different wavelengths (2.02 and 2.09 microns) and two different treatment durations (4 and 8 seconds). In both FIGS. 12 and 13 it will be observed that greater power always corresponds to a greater depth of preferred treatment, although the increase in depth per unit of increased power falls as a function of increasing power. Also, it will be noted that for a given combination of wavelength and power level, a greater treatment duration results in a greater depth of preferred treatment; and for a given treatment duration, the longer wavelength results in a greater increase of preferred treatment depth per unit of increased laser power. Further, it will be noted that, to achieve a desired level of treatment depth, a larger beam pattern necessitates a larger laser power level; that is, for a fixed wavelength and treatment duration, a beam pattern with a greater power intensity will result in a greater depth of preferred treatment.

The curves of FIGS. 12 and 13 represent treatments which result in desirable temperature profiles in the treated regions of the cornea. Typical treatment times at a wavelength of 2.02 microns are in the range of from about 6-8 seconds. For other wavelengths, the computer model may be employed to determine treatment times which result in similar damage profiles in the treated volume of the cornea.

The treatment described in the present invention creates preferential injury within the treated area to the diffusely spread keratocytes, which is followed by cellular response and biochemical synthetic processes. Though the exact mechanism is unknown, the effect of the treatment is thought to cause increased resistance to the internal eye pressure in the treated area and thereby flatten or reduce the curvature of the cornea in the treated area. The present invention creates a form of corneal stromal treatment in which the cellular and biosynthetic process are essentially additive to this pre-existing structure. The effect of keratocyte repopulation and accompanying collagen synthesis might increase tensile strength of the cornea and "stiffen" it. Also, newly synthesized collagen diffusely spread throughout the treated area may provide contractive forces due to formation processes. Additional contractive forces may occur as a result of keratocyte formation, migration and repopulation. It is possible that hypercellularity may occur during repopulation and could contribute to changing corneal curvature. It is also possible that the selective injury of keratocytes affects the glycoproteins surrounding the collagen fibrils. The full refractive effect in rabbits occurs over a time course of about 8 weeks.

It is not known if the specific nature of the biochemical and cellular response is unique to the preferential cellular injury resulting from the treatment. However, as the injury is essentially selective to cells, and the keratocytes are thought to maintain communication with each other, there are probably unique characteristics of the cellular and biochemical synthetic process that result from the unique nature of the treatment. These ideas suggest that there may be an optimum size for the area of cellular damage such that the biochemical and cellular response is rapid and efficient at changing the curvature in the treated area. Treatment patterns such as those described previously in FIGS. 8 and 9 having sectors will affect the net curvature over a wide area while allowing surviving populations of keratocytes proximal to treated areas. The gap between treated areas will not affect the mechanical properties of curvature if the untreated areas are small relative to the total treated area since intraocular pressure will deform the total treated area according to the average resistance over the area.

It is an obvious extension to use such treatment patterns in successive treatments spaced by days, weeks or months to fine tune the corneal flattening required for any given patient. These treatments can increase the total areas of treatment and/or re-treat the same area to provide another sequence of cellular and biosynthetic processes to add to the stroma.

The present invention describes a unique method to change the curvature of the cornea, one which has not been anticipated or suggested by the prior art. The prior art has employed methods in which the treatment directly changes the shape of the cornea, and any biological response subsequent to the treatment has either been incidental to the desired effect or has resulted in undesirable effects such as scarring or light scattering in the cornea. Radial keratotomy involves the making of incisions to intentionally and mechanically weaken the cornea. The incisions lead to a wound healing process which is incidental to the procedure and which leaves small scars. Photorefractive keratectomy involves the ablation of the front surface of the cornea, including a portion of the stroma, to reshape the cornea. In many cases the wound healing response to this procedure results in increased light scattering by the cornea, and in some cases new tissue is formed which diminishes the desired curvature change. To minimize or inhibit these biological responses as much as possible, topical steroidal and nonsteroidal medications are routinely used after this refractive procedure, such medications being known to suppress or inhibit wound healing.

The collagen shrinkage method, as described by Sand, creates regions of the cornea that may exhibit opacity or light scattering, which presumably is why the method currently is not used in the central region of the cornea. This method is generally applied to small areas, often smaller than 1 mm diameter, and the curvature change results from a mechanical communication of force created in a local spot of the cornea. The method is one of immediate physical change in collagen by shrinkage; any subsequent biological response is incidental to the method and is described as not desirable in the art of Sand.

The general biological response to corneal trauma, including cutting, ablation, and collagen coagulation, has been deleterious to the cornea in that scarring has been the typical response. The present invention, however, describes a method to effect a desired biological response in the cornea, most of which occurs subsequent to the treatment, which results in a change in corneal curvature but does not result in scarring or light scattering.

The method of selectively damaging only the cellular components of a treated area suggests several generalizations of the invention. The application of thermal heating by laser irradiation, or any other infrared radiation source of sufficient energy, in combination with biochemical supplements to promote keratocyte activity may be a useful extension of the invention. Biochemical supplements, either topical or systemic are known to promote keratocyte activity; for example, a variety of proteins called epidermal growth factors may be effective in achieving the desired effect.

Another generalization of the present invention employs photochemical methods to selectively necrotize keratocytes. In this case, topical or systemic chemicals can be employed which localize in keratocytes. These chemicals may then be irradiated by light of the appropriate wavelength to initiate cell necrosis by a variety of mechanisms such as free radical chemistry or activation of oxidation processes. Precedent exists for such chemicals to be used in selective necrosis of cancer cells by a method called photodynamic therapy. In a corneal treatment, the selectivity would not be between cancerous and healthy cells, but between keratocyte cells and a relatively inert collagen matrix, and therefore a much greater range of treatment possibilities exists.

A more fundamental generalization of the invention is to activate cellular and biochemical processes in other tissues. In particular, cells with functions similar to keratocytes are found in most tissue. A treatment similar to the current invention in other tissues may provide similar effects, resulting in stronger tissues, removal of local irregularities, or enhanced healing when pre-existing injury is present. Strengthening processes may be activated both in weak tissue and in tissue that has had prior injury or surgical procedures. Typical tissues could include skin, muscle, bone, tendon, nerves and blood vessels. It has generally been recognized that stimulation of a wound healing response would have many potential benefits that are readily obvious, such as quicker healing and stronger union of damaged tissue. But before the present invention there has been no method available to activate an efficacious response which is additive to the pre-existing tissue architecture, through the use of selective cellular injury.

While embodiments and applications of this invention have been shown and described, it would be apparent to those skilled in the art that many more modifications than mentioned above are possible without departing from the inventive concepts herein. The claims, their equivalents, and their equivalent language define the scope of protection. The invention, therefore, is not to be restricted except in the spirit of the appended claims.

APPENDIX I: COMPUTATIONAL MODEL FOR CORNEAL THERMAL EFFECTS

Introduction

An accurate theoretical thermal model is essential to achieve treatment safety, predictability, and reproducibility. We have developed a model that accurately predicts corneal temperatures during and after treatment, and also applies chemical kinetic theory to determine precisely the zones of cellular damage in the cornea. We apply a finite difference computation method to calculate the temperature profile and cellular damage zone in the cornea at any given time, during and after treatment, for a specified laser power, beam profile shape, beam profile size, laser pulse duration, and absorption coefficient.

The fundamental equations for characterizing biological heating were developed by Mainster[1] and have been used by others for studying heating in the cornea[2,3,4,5]. These workers all used the same thermal diffusion model, but because of experimental differences they made slightly different assumptions in applying it. Our model is also based on the thermal diffusion model of Mainster. Like these other workers, we have added refinements and made assumptions which take into consideration our specific operating conditions and which are discussed in the following pages.

The Fundamental Thermal Model

Our thermal damage model employs Mainster's bioheat equation[1] as the theoretical platform and adds the following assumptions:

- The modeling depth is assumed to be a semi-infinite medium with uniform optical and thermal properties throughout (e.g., absorption coefficient, tissue density, heat capacity, thermal conductivity). We model the eye to a 4 mm depth. The cornea itself is approximately 0.52 mm thick. The posterior surface of the cornea is in contact with the aqueous humor, which, like the cornea, is a clear occular medium dominated by water. We therefore assume the entire modeling depth to have like optical and thermal properties.
- These thermal properties are based on the fractional water content of the cornea. This assumption is a refinement of the above referenced work which assumed the corneal thermal properties to be equal to that of water.
- We assume an evaporative/convective boundary at the surface. This is a refinement of the above referenced work and becomes an important factor in our treatment time domain.
- The optical absorption properties of the cornea are equal to that of water. This is consistent with the above references.
- The optical and thermal properties do not change with temperature or laser power density. This is consistent with the above references.
- The laser beam is delivered in a cylindrically symmetric profile, but the intensity can be defined to vary radially if desired.

It is important to note that these assumptions have been developed and empirically validated through comparisons with experimental observations and through self consistency checks over our range of treatment parameters. This process is discussed later in the section entitled "Model Validation and Refinement."

The bioheat equation predicts the tissue temperature at any given time and corneal location. This equation considers two simultaneously occuring processes: the effect of converting laser energy to heat and the effect of thermal diffusion. In cylindrical coordinates with the angular dependence removed, the bio-heat equation is as follows:

$$\partial T/\partial t = (\alpha A_o \exp(-\alpha z))/\rho c + K\{(1/r)(\partial T/\partial r) + (\partial^2 T/\partial r^2) + (\partial^2 T/\partial z^2)\} \quad (1)$$

The first factor in this equation accounts for the conversion of laser energy to heat. The second group of terms determines the effect of thermal diffusion on absolute tissue temperature. T is the temperature in degrees Celcius at a specific corneal radius (r; cm from optical center), depth (z; cm from the corneal surface), and time (t; seconds). $A_o$ is the rate of heat deposition from the laser into a finite area (cal/s cm$^2$) at a specific radius, r, from the center of the cornea. $\alpha$ is the absorption coefficient of the laser light (cm$^{-1}$) for a specific wavelength and is assumed to be that of water[6]. K (cm$^2$/s) is a term which we call the effective thermal conductivity and is defined as follows:

$$K = k/\rho c \quad (2)$$

where p is the tissue density (g/cm$^3$), c is the tissue heat capacity (cal/g °C), and k is the tissue thermal conductivity (cal/cm s °C).

Cooper[7] determined that the heat capacity, the thermal conductivity and the density of biological tissues vary according to their water content in accordance with the following equations (which have been applied here to the tissue in the cornea):

$$c = W + 0.4(1.0 - W) = 0.87 \quad (3)$$

$$k = (13.8W + 1.2)10^{-4} = 0.00119 \quad (4)$$

$$p = 1.0/(W/p_w + C/p_c + E/p_e) = 1.05 \quad (5)$$

where W is the mass fraction of water (0.78 for corneal tissue), C is the mass fraction of collagen (0.15) and E is the mass fraction of extra material in the cornea (0.07)[6]. $p_w$, $p_c$, and $p_e$ refer to the corresponding densities of water, collagen and extra material (1.0, 1.41, 1.06)[8]. The constant K is therefore equal to 0.00131.

Boundary Conditions

A number of boundary conditions must be considered and established when calculating tissue temperatures based on the above fundamental model:

- Boundary at the corneal surface
- Boundary at posterior surface of cornea
- Radial boundary
- Total time over which the computations are made In the work previously cited[1,2,3,4,5] a convective boundary condition was used at the air/cornea interface. This assumption, however, is not valid where heating times are longer than one second. In such instances water evaporation should be considered as an important effect in cooling the outer corneal surface. We have therefore incorporated an evaporative/convective surface boundary condition in our model.

The evaporative/convective boundary condition has been analyzed in many problems related to chemical engineering[9]. It assumes that heat is lost as a result of evaporation from a surface and that enough air motion is present above the evaporative layer for convection to take place as well. The result from this work shows that the heat loss at this boundary is proportional to the enthalpy of vaporization, a mass transfer coefficient, and the difference between the humidity of air at the evaporative surface and the humidity of ambient air.

More specifically, the evaporative/convective heat loss can be calculated as follows:

$$H_{ev} = k_y MW_{air} \Delta H_{vap} \alpha (H - H_o) \quad (6)$$

$H_{ev}$ is defined as the heat loss (cal/s cm$^3$); $k_y$ is the mass transfer coefficient ($\approx 0.001$ moles s$^{-1}$ m$^{-2}$ for air/water mixtures); $MW_{air}$ is the molecular weight of air (g); $\Delta H_{vap}$ is the heat of vaporization of water (570 cal/g at 48° C. and approximately constant with temperature); $\alpha$ is the absorption coefficient (cm$^{-1}$) of the laser light for a specific wavelength (assumed to be that of water); H is the humidity of air at the evaporative surface (where the vapor pressure of water=p); $H_o$ is the humidity of ambient air before vaporization (0.01; equivalent to 60% relative humidity at 22° C.). H, the humidity of air at the evaporative (corneal) surface, must be calculated and is a function of the vapor pressure of water as follows:

$$H = \{MW_{water}/MW_{air}\}\{p/(P-p)\} \quad (7)$$

where MW is the molecular weight, p is the vapor pressure of water at temperature T (temperature in °C. at the corneal surface) and P is the atmospheric pressure (760 mm Hg). The vapor pressure of water (p) is a function of temperature, T, and also must be calculated:

$$p = p^* \exp\{(-\Delta H_{vap}/R)[(1/T)-(1/T^*)]\} \quad (8)$$

where $\Delta H_{vap}$ is the heat of vaporization of water at p* and T* and R is the gas constant (8.314 Joules/°K. mol). p* is the vapor pressure of water (83.71 mm Hg) at T* (48° C.). Values of p* and T* were selected to allow valid extrapolation of p at temperatures exceeding 80° C.

In our model, we use these equations to determine the evaporative/convective heat loss ($H_{ev}$). For the surface layer, this heat loss is subtracted from the laser heat deposition with the net effect then used in our fundamental thermal model.

The remaining three boundary conditions are conventional and much easier to select. A boundary condition of a constant temperature was assumed at a depth (z) of 4 mm and a radius (r) of 6-8 mm (dependent upon the size of the beam profile). These assumptions result in consistent and stable mathemetical results over the corneal profile.

The last boundary condition is the total time over which the computations are made. We have selected a time frame where the temperature has fallen below that which produces significant biological effects. This time is nominally 50% longer than the total laser heating time since the temperature drops rapidly after the laser heating is completed due to thermal diffusion.

Cellular Damage Model

Our fundamental thermal model allows us to determine temperature as a function of treatment parameters, but we are also interested in modeling the effects of these thermal changes at the cellular level. Cell damage is essentially a kinetic phenomenon in which the rate of cell damage depends largely on temperature and in which the critical temperature for thermal damage is a function of the heating time[10]. It is this time/temperature function which dominates the cell damage process.

Historically, the rigorous ideas of molecular kinetics have formed the basis of an empirical model of cellular damage kinetics. Henriques[11] was the first to propose such a model for a biological system and Birngruber[12] refined it. Others have since used it in modeling thermal processes in the eye[4,13]. This model defines the rate constant (k) for the cellular damage process as a simple Arrhenius expression.

$$k = A \exp(-E/RT) \quad (9)$$

where k is the cellular damage per unit of time, E is an empirical activation energy for the cellular damage process, R is the ideal gas constant, T is the temperature, and A is the pre-exponential term. "A" is often represented in terms similar to chemical kinetics.

$$A = (k_b T/h)(\exp(\Delta S/R)) \quad (10)$$

where $k_b$ is Boltzmann's constant, h is Planck's constant, R is the ideal gas constant, T is temperature and $\Delta S$ is the activation entropy.

The activation energy (E) is often converted to an activation enthalpy, $\Delta H$, and the rate constant for the cellular damage process then becomes $$k = \{k_b T/h(\exp(\Delta S/R))\}\{\exp(31 \Delta H/RT)\} \quad (11)$$

66 H and $\Delta S$ are empirically determined and are specific to the type of cell being studied. By comparing histological results with model predictions, we have derived values of $\Delta H = 150$ kcal/mol and $\Delta S = 380.5$ cal/K mol for both keratocytes and endothelial cells. The derivation of these values is discussed in a later section, "Model Validation and Refinement."

The application of the above equations defines a cellular damage parameter, $\Omega$, where the rate is written as a time derivative $$d\Omega/dt = k = \text{cellular damage per unit time} \quad (12)$$

Computing the value of $\Omega$ for any time dependent change in temperature requires an integral of this relationship.

$$\Omega = \int d\Omega = \int k\, dt \quad (13)$$

$$\Omega = \int \{k_b T/h \, (\exp(\Delta S/R))\}\{\exp(-\Delta H/RT)\}dt \quad (14)$$

By selecting a time increment, dt, which is very small, the temperature during that time increment is effectively constant. $d\Omega$ can then be calculated using equations #11 and #12 with the time increment, dt, and the constant temperature (T) during that time increment. The integral in equation #13 is finally determined by summing all the $d\Omega$ over the total treatment time. This is the principle of a finite difference computation method.

In our computer program, the temperature (T*) in a given volume element of the cornea is calculated for an increment of time, dr, using our fundamental thermal model (bioheat equation). $d\Omega$ for that volume element is then determined by simply multiplying k* by dt. k* is calculated using equation #11 where T=T*.

$\Omega$ for a given volume element is calculated by summing all the $d\Omega$ for that volume element over all dt throughout the time course of the treatment heating and cooling. The final result is a set of values for $\Omega$ which correspond to each volume element of the total corneal volume profile.

$\Omega$, as calculated in our computer program, gives a precise numerical value for cellular damage for specific values of ΔH, ΔS and a set of operating parameters. But, remembering that this is an empirical model, it is the correlation of numerical values of Ω with histology which gives Ω its real meaning. Henriques tested this model for the thermal denaturation of protein in pig skin and observed that, for his selection of ΔH and ΔS, a Ω of 1.0 was the 1/e point of cell necrosis, or the point when 63% of the cells had died. A Ω of 0.53 indicated the threshold of irreversible thermal damage.

We have histologically examined zones of treatment in order to correlate Ω with specific biological effects in the cornea. We observed a threshold of irreversible cellular damage where Ω=0.5. This value (Ω=0.5) serves as our definition for the threshold of irreversible keratocyte and endothelial cell damage. It is used throughout our work to predict damage to corneal cells as a function of treatment parameters.

To illustrate the dependence of cellular damage on time and temperature, we provide below the example of a treatment where temperature remains constant over the duration of the treatment. This example is hypothetical in that constant temperature treatments would not occur in the real world where treatment times of more than about one second would lead to significant thermal diffusion. However, the simplicity of this illustration is helpful for intuitive purposes. For a constant temperature, the integral in equation #13 is simplified.

$$\Omega = k^* \tau \qquad (15)$$

where k* is the rate constant for cellular damage at a constant temperature and τ is the total time over which the temperature is held constant. The table below compares the temperatures required to reach the corneal cellular damage threshold (Ω=0.5) for the indicated times, as calculated with equations #11 and #15. There is a dramatic dependency of the damage threshold temperature on time within this parameter range.

Time for irreversible thermal damage to occur at a fixed treatment temperature:

| Time (seconds)   | 60    | 8     | 3     | 1     | 0.1   |
|------------------|-------|-------|-------|-------|-------|
| Temperature (°C.) | 61.25 | 64.24 | 65.72 | 67.39 | 70.95 |

Computation Method

Just as the fundamental equations for corneal heating are well understood, so are the proper mathematical methods for obtaining valid solutions. Solving differential equations using simple finite difference techniques is a well proven approach. Our computer program calculates the temperature throughout the cornea over a selected timeframe using a finite difference method. In this method, we select small increments of time, radius and depth. These computation grid increments can be selected by simply comparing results derived from progressively finer dimensions until mathematical stability is achieved. We have found increments of 1 msec., 0.01 cm., and 0.0025 cm. (for time, radius and depth, respectively) to yield stable results.

Our computer program employs a simple iterative loop over time, with each time increment being used for adjusting temperature as a result of thermal diffusion heat losses, evaporative/convective cooling, and heat deposition by the laser. For a given time increment the computation grid begins at the surface of the cornea and works radially from the center point. The heat loss due to water evaporation from the surface layer is subtracted from the laser heat deposition (see "Boundary Conditions") profile. The temperatures over the corneal surface are then calculated. The program then works progressively deeper into the cornea. The temperature (T) and cellular damage parameter (dΩ) at each grid location are calculated and used in the next iteration. The program works until the boundary conditions for the radius, depth and time (discussed above) have been fulfilled. Ω for each grid location is calculated by summing all the dΩ determined for each time increment in the computation. Various plots are then generated from the computed results.

A detailed flow chart of the program is illustrated in the following figure.

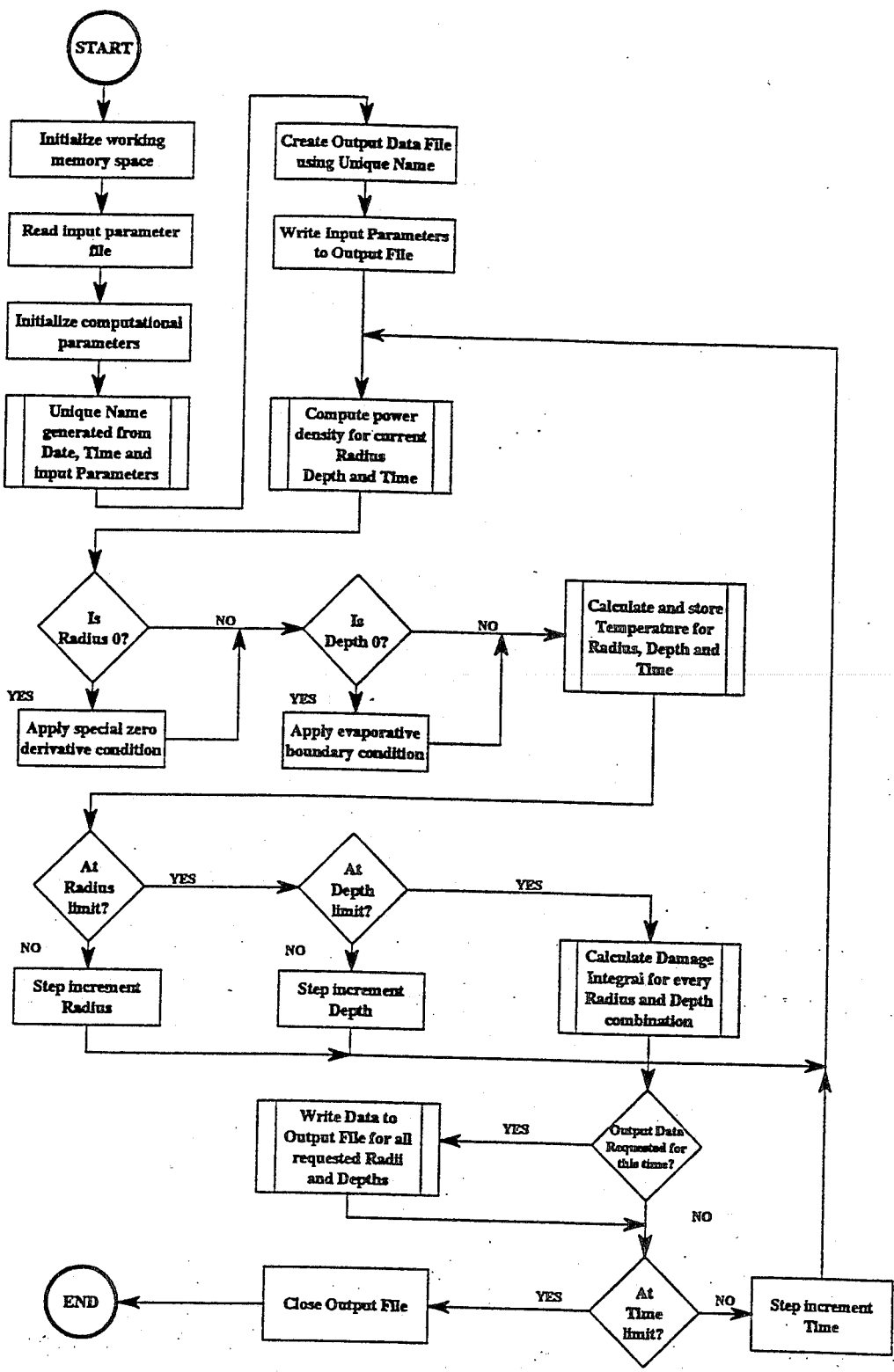

Output Generated From the Model

When providing inputs to our model, we also specify the increments of time, radius and depth for purposes of program output; these increments of measurement are larger than those used by the model in its actual computation. Using these specified output parameters, the program stores the values of temperature (T) and the cellular damage parameter ($\Omega$). The resultant product is a matrix of T and of $\Omega$, both as a function of corneal location (r,z) and time. This data can be plotted in four forms which we find useful for visual interpretation of the results.

To illustrate this output we use an example of a flat beam profile (nominally 4.5 mm in diameter), a treatment duration of 8 seconds, a laser power of 0.8 watts, and a wavelength of 2.02 microns. The figures which follow show the beam profile and two of the plots produced from our model analysis. These plots are typical of the treatment profiles generated in many of our treatments. There is a characteristic temperature gradient from the front to the back of the cornea. It is this temperature gradient which will allow us to protect the endothelium from thermal damage. The profile is hottest in the optical center with a temperature gradient sloping radially outwards, typical of a flat beam profile. The plot of radius versus depth shows a contour of the treated corneal tissue which experiences irreversible cellular damage. The area of cellular damage is largest at the corneal surface and decreases at greater depths. The deepest point of cellular damage is clearly depicted in this type of plot. For this example, we achieve cellular damage to a depth of 0.5 mm, just short of the human endothelium which is located at a depth of approximately 0.57 mm.

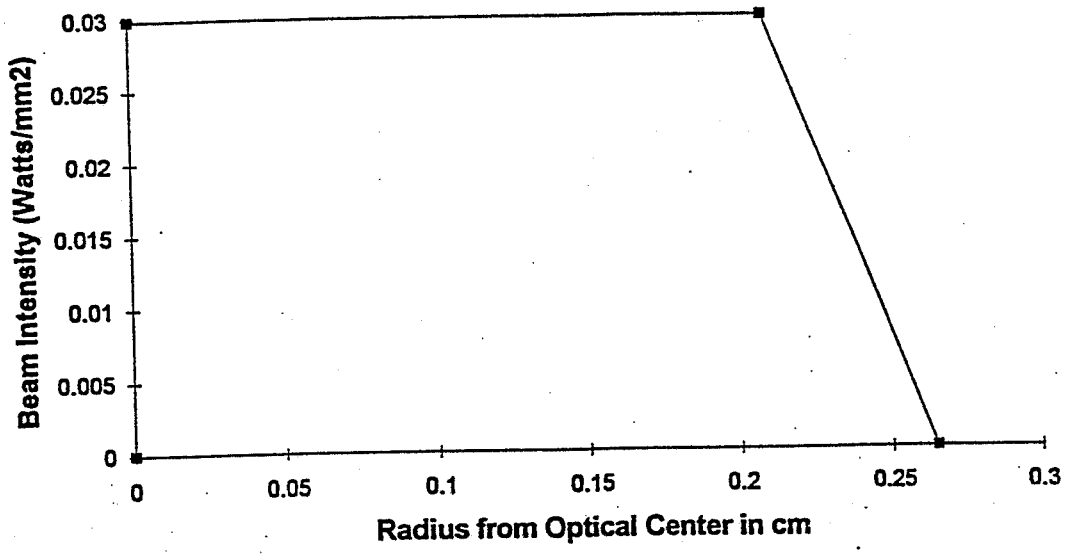

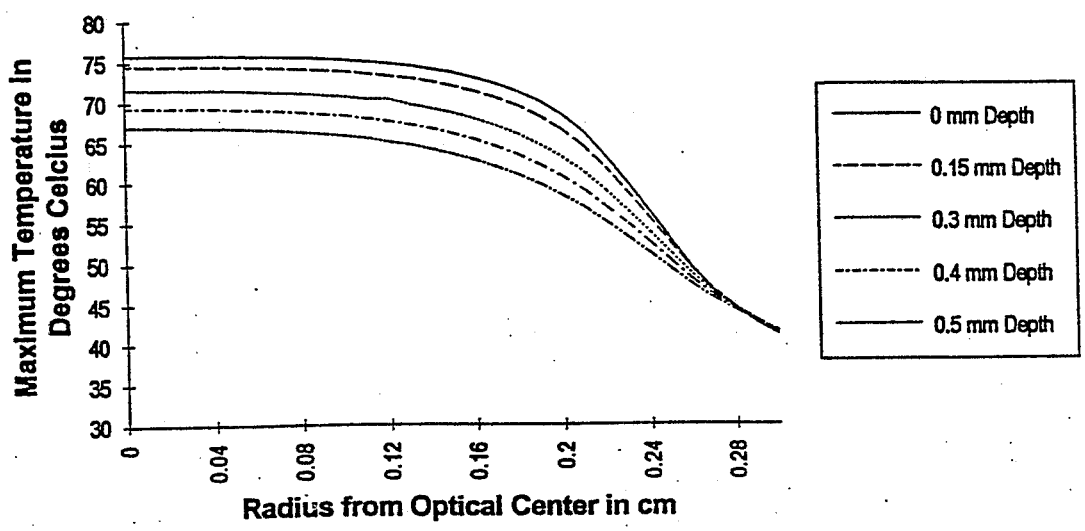

Tissue Profile of Irreversible Thermal Damage
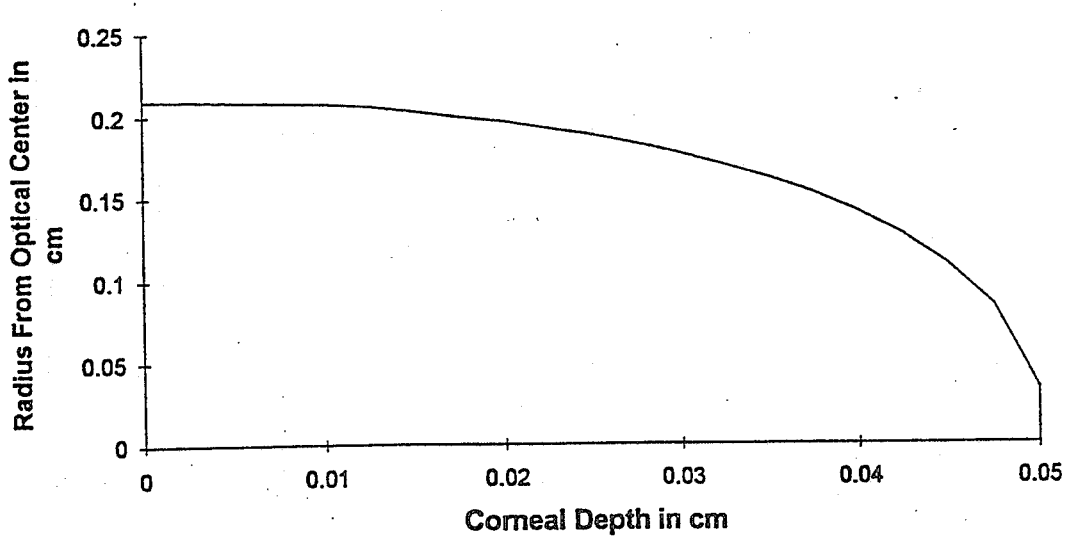
COMPARISON OF MICROTHERMOCOUPLE MEASUREMENTS
WITH MODEL CALCULATIONS
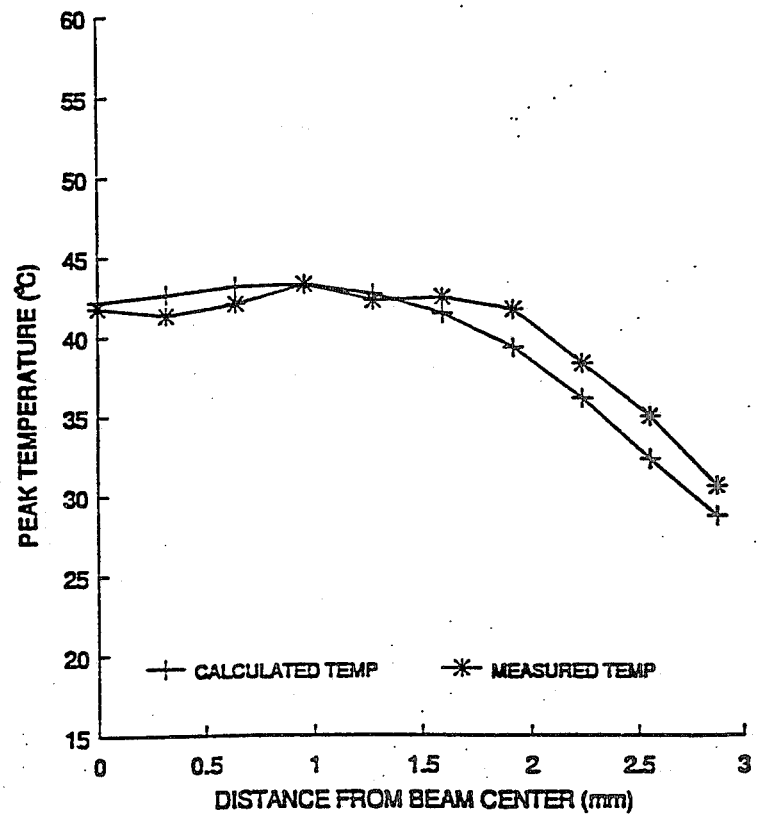

COMPARISON OF MICROTHERMOCOUPLE TEMPERATURE MEASUREMENTS WITH MODEL CALCULATIONS

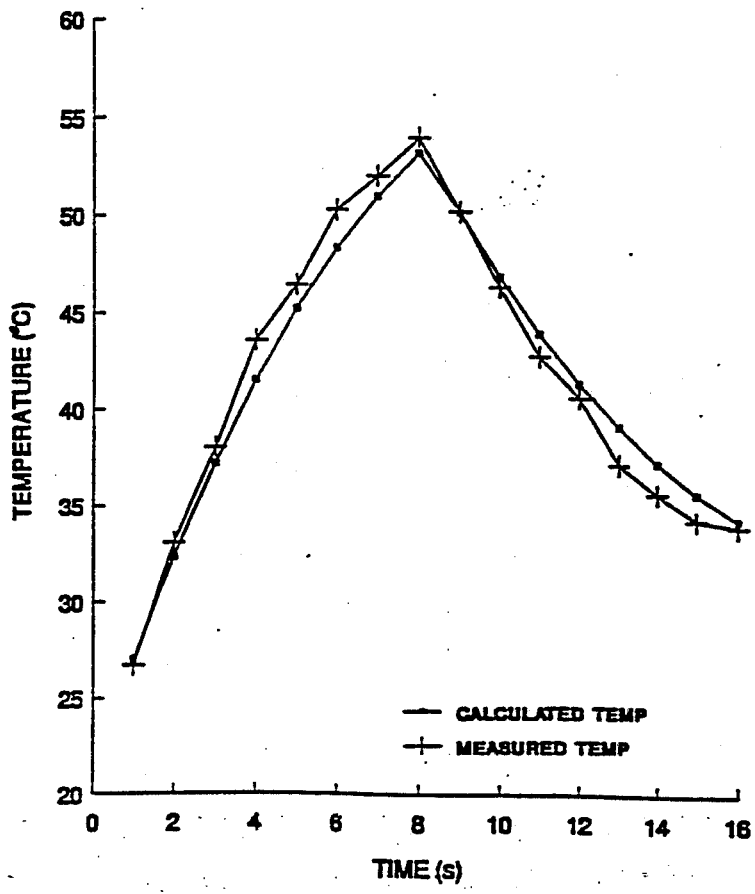

Model Validation and Refinement

A number of experiments were conducted to refine and validate our corneal thermal model:
Temperature calibration using corneal phantoms
Temperature calibration through comparison with literature data
Comparison of cellular damage calculations with experimentally determined cellular damage thresholds A corneal phantom was used to determine absolute temperatures via microthermocouple measurements. The phantom was cast from an agarose gel containing 10% glycerol for stability at higher temperatures. Temperatures were measured with a copper constantan microthermocouple with a diameter of 0.025 mm, a length (recording depth) of 0.076 mm, and a time constant of 0.002 seconds.

These measurements determined absolute temperatures at various radial distances from the beam center. Depth dependent measurements would be very difficult to do with any precision because of the difficulties in accurately measuring depths. We therefore positioned the microthermocouples just below the phantom surface and utilized a wavelength (1.86 microns; $\alpha=11$ cm$^{-1}$) that minimized temperature variations over depths the size of our microthermocouple. The temperature gradient across a 0.5 mm depth was 3 degrees at our greatest test powers. This means that our thermocouple recording depth of 0.076 mm gave a recording uncertainty of about 0.5 degrees C in the worst case.

The typical test used a thin saline film over the outer surface of the phantom, similar to our treatment conditions. Time dependent measurements were made at a sampling interval of 0.10 sec. over a total time of 8 to 10 seconds with laser powers of 0.45 to 0.84 watts. Heating was studied for up to a 30 degree temperature increase. An example is shown in the following figures where the model and data are compared as a function of distance from the beam center and as a function of time. The model and experimental values are in close agreement. We consider one degree C to be the accuracy of this particular experiment when considering the measurement errors and possible errors in the thermal conductivity of the phantom (calculated from literature data). It is interesting to note that the computer model would predict a temperature 4 degrees higher if the typical convective boundary condition were used instead of our evaporative/convective boundary condition. This indicates that the model correctly predicts evaporative cooling effects.

A second check on the model's ability to accuractely calculate temperatures used the data of Bargeron, et al[ref]. This group measured temperatures at the endothelium in excised rabbit corneas upon irradiation by a $CO_2$ laser ($\alpha=950$ cm$^{-1}$). The heating took place over intervals of 0.104 and 1.04 seconds. Using our model, we calculated temperatures for Bargeron, et al's operating parameters and achieved agreement with their data to an accuracy of 1 degree for both exposure times. Interestingly, for the 1.04 second exposure, the evaporative boundary condition of our model was very important, and with the convective boundary condition (used by Bargeron and also checked by us) the temperature was computed to be 5 degrees higher than measured. This comparison enhanced our confidence in the accuracy of the model for actual corneal conditions when evaporative cooling is significant. It is important to note that this wavelength (10.6 microns, $\alpha=950$ cm$^{-1}$) has a short depth of laser light absorption and, therefore, there is a large thermal gradient in the cornea. These conditions are a good test for the evaporative cooling model.

The next step in refining and validating our model was to compare our cellular damage calculations ($\Omega$) with experimentally determined cellular damage thresholds. This process was initially used as a method of defining $\Delta H$ and $\Delta S$, the kinetic activation parameters for the cornea. Recall, from equation #14, that $\Delta H$ and $\Delta S$ are used in calculating values for $\Omega$. We have found no such literature values for corneal cells, but literature values for $\Delta H$ were documented for fundus cells[13], HeLa cells[16], and dermis cells[11,17]. These values provided us with a starting range.

We began by observing histological measurements of endothelial damage areas and keratocyte damage areas created by our treatment. The histology indicates that, in our strong treatments, the zone of damage is essentially identical for endothelial cells and keratocytes near the endothelial layer. We also observed a continuous zone of damage from the anterior to the most posterior point in the cornea. We therefore assumed that the damage parameters are essentially identical for both endothelial and keratocyte cells. This assumption is supported by the findings of McCally[18].

We proceeded to histologically measure the power threshold of endothelial damage for exposure times ranging from 2–8 seconds (see section 2.3.3 in our original IDE submission for histology protocol). Using these threshold operating conditions, we then iteratively tested various values of $\Delta H$ and $\Delta S$ in the calculation of $\Omega$. We looked for combinations of $\Delta H$ and $\Delta S$ which gave us equivalent values of $\Omega$ under these threshold operating conditions. Over such a narrow range in treatment conditions there is no unique solution for these parameters since they can compensate each other to some degree. The exact value of $\Delta H$ is less important than selecting a suitable $\Delta S$ to match a given estimate, since this model is empirical and therefore is most valid for use within a range of times that have been empirically tested. Therefore, we have selected a value of 150 kcal/mol for the activation energy and a value of $\Omega=0.5$ for the threshold of irreversible cellular damage (consistent with convention established in the literature). We then calculated the activation entropy ($\Delta S=380.5$ cal/K mol) to give good agreement with our histology for exposure times in the 2–8 second time range.

Summary

This model has proven invaluable in characterizing the tissue effect produced by our treatment for a specific set of operating parameters. It has allowed us to understand the treatment sensitivity to variations over a broad parameter space. It has also allowed us to scale our operating parameters to different wavelengths and beam profiles, and to the thicker corneas of primates. The process of refining this model with feedback from our histological findings, our temperature measurements and the measurements of others, has produced a valid thermal model with proven self consistency. This model will provide us with an important level of control and predictability in accomplishing our human clinical work.

REFERENCES

[1] Mainster M. A., White T. J., et al. Transient thermal behavior in biological systems. Bull Math Biophysics 1970; 32:303–314.

[2] Mainster M. A., White T. J., et al. Corneal thermal response to the $CO_2$ laser. Applied Optics 1970; 9 (3):665–667

[3] Mainster M. A. Ophthalmic applications of infrared lasers—thermal considerations. Invest Ophthalmol Vis Sci 1979; 18:414–419

[4] Takata A. N., et al. Thermal model of laser induced eye damage. IIT Research Institute. Final Tech. Rep. F-41609-74-C-0005; 1974.

[5] Egbert D. E., Maher E. F. Corneal damage thresholds for infrared laser exposure: empirical data, model predictions and safety standards. Brooks AFB: USAF School of Aerospace Medicine. Rep. SAM-TR-77-29; 1977.

[6] Curcio J. A., Petty C. C. The near infrared absorption spectrum of liquid water. Journal of the Optical Society of America 1951; 41 (5): 302–304.

[7] Copper T. E., Trezek G. J. Correlation of thermal properties of some human tissue with water content. Aerospace Medicine 1971; 42 (1): 24–27.

[8] Worthington C. R. The structure of the cornea. Quarterly Review of Biophysics 1984; 17:423–451.

[9] Geankoplis C. J.: Transport Processes and Unit Operations. Newton, Mass.: Allyn and Bacon, Inc; 1983.

[10] Peppers A., Vassiliadis A., Dedrick K. G., et al. Corneal damage thresholds for $CO_2$ laser irradiation. Applied Optics 1969; 8:377–381.

[11] Henriques F. C. Studies of thermal injury. Arch Pathol 1947; 43:489–502.

[12] Birngruber R., Hillenkamp F., Gabel V. P. Theoretical investigations of laser thermal retinal injury. Health Physics 1985; 48:781–796.

[13] Vassiliadis A., Zweng H. C., Dedrick K. G. Ocular laser threshold investigations. USAF School Aerospace Med., Brooks AFB, TX. Rep. AD731577; 1971.

[14] Bargeron C. B., Farrell R. A., Green W. R., McCally R. L. Corneal damage from exposure to IR radiation: rabbit endothelial damage thresholds. Health Physics 1981; 40: 855–862.

[15] Bargeron C. B. McCally R. L., Farrell R. A. Calculated and measured endothelial temperature histories of excised rabbit corneas exposed to infrared radiation. Exp Eye Res 1981; 32:241–250.

[16] Moussa N. A., McGrath J. J., et al. Kinetics of thermal injury in cells. J Biomech Engr 1977, August:1-55–159.

[17] Takata A. N., Zaneveld L., Richter W. Laser-induced thermal damge in skin. USAF School Aerospace Med., Brooks AFB, TX. Rep. SAM-TR-77-38, 1977.

[18] McCally R. L., Bargeron C. B., Green W. R., Farrell R. A. Stromal damage in rabbit corneas exposed to $CO_2$ laser radiation. Exp. Eye Res. 1983; 37:543–550

```
C
C       FILE NAME:  CALC3.FOR    LAST CHANGE DATE: 5/4/94
C       VERSION WITH BINARY WRITE OF ALL INPUT PARAMETERS
C       POWER PROFILE WITH LINEAR INTERPOLATION DONE
C
C-------------------------SUMMARY------------------------------
C       THIS PROGRAM USES FINITE DIFFERENCE APPROXIMATIONS
C       TO MODEL CORNEAL HEATING BY INFRARED LASER APPLI-
C       CATION.  AT LONG EXPOSURE TIMES, THE BIO-HEAT
C       EQUATION CAN BE USED TO MODEL DIFFUSION IN THE
C       CORNEA. THE BOUNDARY
C       CONDITIONS ARE SUCH THAT THERE IS NO TEMPERATURE
C       CHANGE AT THE EDGE OF THE CYLINDER OR AT THE BACK
C       OF THE CYLINDER.  THERE IS A CONVECTIVE BOUNDARY
C       AT THE SURFACE OF THE EYE AND A ZERO DERIVATIVE
C       BOUNDARY AT THE CENTER OF THE CYLINDER.  THE
C       OCULAR SURFACE IS ASSUMED TO BE FLAT, AND THE
C       THERMAL PARAMETERS USED ARE CORRECTED FOR
C       THE 75% WATER CONTENT OF THE CORNEA.
C
C
C*************** VARIABLES NEEDING INPUT *************************
C
C       ---------------FILE HANDLING VARIABLES-----------------
C       ROOTNM, CHARACTER VARIABLE OF 6 LENGTH
C       NTWO, INTEGER VARIABLE FROM 10-99 THAT IS ADDED TO THE NAME.
C------------------------------------------------------------------
C-------------EXPLANATIONS OF FILE HANDLING VARIABLES, -----------
C       WE NEED A NAME OF 6 CHARACTERS (ROOTNM) IN THE INPUT FILE THAT
C       WILL BE THE FIRST 6 OF THE OUTPUT FILE, TO WHICH IS ADDED TWO
C       ASCII CHARACTERS EQUAL TO THE INTEGER NUMBER (10-99) NTWO.
C       PROVISION IS MADE TO HANDLE <6 CHAR BY ADDING 'X' TO MAKE 6.
C       ERRORS IN NTWO NOT BEING 10-99 STILL GIVE USEFUL FILE NAMES.
C
C       EACH INPUT DATA SET WOULD HAVE A ROOTNM AND NTWO DESIGNED TO
C       PROVIDE A UNIQUE FILE NAME WITH EXTENSION OF .BIN FOR BINARY
C       (OR .ASC FOR ASCII OPTIONS).  THE NAME IS CREATED BY THE
C       SUBROUTINE NAM6P2(NBASE,NTWO,EXT,NAME) WHICH CALLS
C       SUBROUTINE TWOCHR(NTWO,ASCNUM)
C
C       ---------------ALL OTHER COMPUTATIONAL VARIABLES----------------
C       WE ASSUME THAT ALL INPUT DATA IS READ FROM A FILE, AND MULTIPLE
C       COMPUTATIONS COULD BE DONE WITH AUTOMATIC DEFINITION OF OUTPUT
C       FILES, USING INFORMATION IN THE INPUT FILE.  THE INPUTS WILL BE
C       IN ASCII, IN FREE FORMAT, AS IF IT IS A CONSOLE INPUT.  THE DOS
C       COMMAND LINE WILL REDIRECT (<) THE PROGRAM TO USE A FILE INSTEAD
C       OF THE CONSOLE. E.G., C:\DOS4GW BVERS2 <INPUT
C
C       -------------ALL COMPUTATIONAL VARIABLES-------------------
C
C       THE DZ IS THE Z DIRECTION STEP-SIZE IN CM.  Z IS PERPENDICULAR
C       THE DR IS THE RADIAL DIRECTION STEP-SIZE IN CM.
C       THE DT IS THE TIME STEP IN SECONDS
C       THE ZTOT IS THE Z DIRECTION, TOTAL THICKNESS IN CM
C       THE RTOT IS THE R DIRECTION TOTAL RADIUS IN CM
C-TYP-DATA DZ /0.008/, DR /0.016/, DT /0.010/, ZTOT/0.4/, RTOT/0.8/
C
C       ALPHA IS THE ABSORPTION COEFFICIENT IN 1/CM
C       HUMID, RELATIVE HUMIDITY OF AIR OUTSIDE OF CORNEA, SEE VAPOR SUBR
C       TAIR, TEMPERATURE OF AIR OUTSIDE OF CORNEA, IN DEG. C.
C       TCORN, TEMPERATURE OF CORNEA, IN DEG. C.
C       TTOT, THE TOTAL TIME FOR THE CALCULATION TO BE APPLIED
```

```
C
C                -------------LASER RELATED VARIABLES (POWER)--- ---------------
C         PWR,   LASER POWER IN WATTS FOR THE COMPLETE PATTERN ENTERING THE
C                CORNEA, THE DISTRIBUTION IS ALWAYS NORMALIZED TO POWER.
C         NDIST, AN INTEGER THAT SELECTS THE POWER DISTRIBUTION FROM THE SET
C                LISTED IN SUBROUTINE POWER. SEE POWER TO CHECK CHOICES.
C         NDIST=1,
C                THIS SELECTS A PIECEWISE FITTED DISTRIBUTION DEFINED BY
C                LINEAR SEGMENTS OF STRAIGHT LINES.
C                THE VARIABLES ARE GIVEN FOR FOUR INCREMENTS.
C                THE RJ(1) IS AN OUTER RADIUS SO R .GE. HAS ZERO POWER
C                THE BB(I) ARE INTERCEPTS DEFINED BETWEEN RJ(I) AND RJ(I+1)
C                THE SL(I) ARE SLOPES FOR THE SAME LINES.  RJ(5) =0
C
C                -------------LASER RELATED VARIABLES (TIME)------------------
C         THEAT, A TIME FOR THE HEATING PULSE TO BE APPLIED, IN SECONDS,
C                THIS ASSUMES ONE PULSE IN THE TREATMENT.
C
C****************DATA INTERVALS TO BE RECORDED IN THE OUTPUT FILE******
C
C      THE PRIMARY SELECTION OF WHEN TO WRITE COMPUTED DATA IS BY TIME
C      THE INPUT VARIABLES ARE:
C      TMIN, THE STARTING TIME IN SECONDS CONVERTED TO AN INTEGER
C             NUMBER OF INCREMENTS.   LMIN=NINT(TMIN/DT)
C      TMAX, THE ENDING TIME.         LMAX=NINT(TMAX/DT)
C      TINCR, THE INCREMENT TIME.   LINCR=NINT(TINCR/DT)
C      IT IS CLEAREST IF INTEGRAL MULTIPLES OF DT ARE PICKED
C      THE NINT FUNCTION (NEAREST INTEGER) PREVENTS ERRORS.
C
C      THE LOOPS ARE FIRST DEFINED BY Z, THE DEPTH.
C      ZMIN, THE STARTING VALUE OF Z, IN CM (MULTIPLE OF DZ)
C      ZMAX, THE MAXIMUM VALUE OF Z, IN CENTIMETERS
C      ZINCR, THE INCREMENT OF Z, SHOULD BE A MULTIPLE OF DZ
C      THE VALUE OF ZMAX SHOULD BE AN INTEGRAL MULTIPLE OF DZ*ZINCR
C      NOTE THAT ZMIN, ZMAX NEED TO BE INCREASED BY 2 TO DEFINE LOOPS
C
C      THE INNER LOOP IS DEFINED BY R, THE RADIUS
C      RMIN, THE STARTING VALUE OF R, IN CM. (MULTIPLE OF DR)
C      RMAX, THE FINAL VALUE OF R, IN CM.
C      RINCR, THE INCREMENT OF R, SHOULD BE A MULTIPLE OF DR.
C      THE VALUE OF RMAX SHOULD BE AN INTEGRAL MULTIPLE OF DR*RINCR
C      NOTE THAT RMIN, RMAX NEED TO BE INCREASED BY 2 TO DEFINE LOOPS
C
C*************** FILE SPECIFICATIONS **********************************
C
C      USE STRAIGHT BINARY WRITING, BLOCKSIZE IS
C      AN EXTENSION OF WATCOM F77 AND IS NOT REQUIRED SINCE 4K DEFAULT.
C      BLOCKSIZE IS AN EXTENSION TO F77 FOR REDUCING FREQUENCY
C      OF DISK TRANSFERS.  SHOULD BE TRANSPORTABLE WITHOUT BLOCKSIZE.
C-------------------MOST GENERAL FORMAT---------------
C-EG--OPEN(UNIT=NOUT, FILE=NAME, FORM='UNFORMATTED')
C-----THIS TYPE OF BINARY SHOULD BE TRANSPORTABLE
C-----HOWEVER SMALLER FILES FROM WATCOM SPECIFIC FORMAT BELOW
C
C---------------------SHORTEST BINARY FILES IN WATCOM-----------------
C      SHORTEST FILES USE F77 EXTENSION OF WATCOM, WHERE RECORDTYPE=
C      'FIXED' CAUSES OMISSION OF TWO EXTRA RECORD LENGTH SPECIFIERS,
C      FILE WILL BE SHORTER BY 2x4=8 BYTES/WRITE STATEMENT IN WATCOM.
C      THE FILE STRUCTURE FOR A 7 ITEM WRITE STATEMENT IS 7x4=28 BYTES
C      THE RESULTING FILE IS A FIXED BINARY STRUCTURE.
C---------------------------------------------------------------------
C-------------------------OPEN TO WRITE THESE FILES-------------------
```

```
C----U      RECORDTYPE='F1  )',BLOCKSIZE=32768)
C              IX∈ ),
C-----------------------TO READ THESE FILES-----------------------
C     OPEN(UNIT=M,FORM='UNFORMATTED',ACCESS='DIRECT',FILE=NAME,RECL=28)
C     READ(M,REC=I) TIME,R,Z,TMP,OM1,OM2,EVAP   [SET UP A DO LOOP ON I)
C-----------------------------------------------------------------
C
C*****************************************************************
C********** STABILITY CRITERIA FOR SOLUTION **********************
C     THE INCREMENTS MUST BE CONSISTENT WITH THE ALPHA, THAT IS, THE
C     STEP SIZE ON Z MUST BE SMALLER THAN ABOUT 1/10 THE VALUE OF 1/ALPHA
C
C     THE SELECTION OF DZ AND DR MUST BE SELF CONSISTENT WITH DT.  THE
C     CRITERIA IS:
C     DT*K*( 1/DZ**2 +1/DR**2 ) .LE. 0.5
C
C*****************************************************************
C*******************START OF FORTRAN STATEMENTS*******************
C*****************************************************************
C
C*************** SETUP ARRAY DIMENSIONS **************************
      DIMENSION V(202,202),VN(202,202),DINT1(202,202),DINT2(202,202)
      DIMENSION PD(202),A(202),EVAPX(202),RJ(5),BB(4),SL(4)
C
C     THE DIMENSIONS ARE SOMEWHAT ARBITRARY, AND FOR THE GIVEN DEPTH
C     AND RADIUS WE ESTIMATE A DIMENSION SIZE SIMILAR TO THE LARGEST
C     NUMBER+2 OF INCREMENTS IN Z OR R.  THIS COULD BE A PROBLEM IF THE
C     MAXIMUM RADIUS, RTOT, AND MAXIMUM Z DIM, ZTOT, ARE LARGE
C
C*************** DEFINE VARIABLES *****************
C
      REAL K
C
      CHARACTER NAME*12,ROOTNM*6,EXT*3, TFILL*2
      INTEGER*2 YEAR,MONTH,DAY,HRS,MINS,SECS,HSECS
C
C     DEFINE VARIABLES FOR GETDAT AND GETTIM
C*****************************************************
C
C******************SYSTEM VARIABLES****************
C
C     SYSTEM VARIABLE, PICK UNIT NUMBER FOR OUTPUT
      NOUT=10
C     SYSTEM VARIABLE, PICK CONSOLE INPUT AS UNIT=5 FOR WATCOM
      NC=5
C     TWO BYTE CONSTANT USED FOR FILLING WRITE BUFFER
      TFILL='XX'
C
C*************** DEFINE VARIABLES THAT ARE FIXED FOR CORNEA*********
C
C     THE SYMBOL K IS USED FOR EFFECTIVE THERMAL CONSTANT
C     COEFF OF HEAT TRANSFER (H), AND EFFECTIVE THERMAL
C     CONDUCTIVITY (K); UNITS WITH: CAL, CM, DEG C, AND SEC
C     THE EFFECTIVE K=k/rho/heat cap   see JES thesis p102
C     rho=1.066, k=.00116, C=0.85
C
      H=7.0E-04
      K=0.00128
C
C*****************************************************************
C***********************INPUT OF ALL VARIABLES********************
C*****************************************************************
```

```
C       NBATCH=1, MEANS ONE   A SET              (←DATA)            (←INPUT)
C       NBATCH= , THE TOTAL NUMBER OF DATA SETS IN THE INPUT FILE
C                 A data set includes the line with root names and all
C                 following data lines
C       NBATCH IS on THE FIRST line of THE INPUT FILE , ONLY ENTER ONCE
C
C       REUSE=1 (YES), MEANS THAT COMMON DATA INPUT IS RE-USED FROM PRIOR SET
C       REUSE=0 (NO), MEANS THAT ALL DATA IS READ IN FOR EACH DATA SET.
C
C       SET INITIAL COUNTER ON THE NUMBER OF DATA SET READS
C       RETURN FOR NEXT DATA READ IS AT STATEMENT 1020
C
        READ(NC,*) NBATCH
        NCNTB=NBATCH
 1000   READ(NC,*) ROOTNM, NTBEG,NTFIN, ALPHA,REUSE
        NCNTB=NCNTB -1
        NCNT=0
        NCNTG=NTFIN -NTBEG +1
        numid=ntbeg
C
 1010   READ(NC,*) NDIST, PWR, THEAT
C
        NCNTG =NCNTG-1
C
        IF (NCNT .EQ. 0   .OR. REUSE .EQ. 0.0) THEN
                    NCNT = 1
                    READ(NC,*) DZ, DR, DT, ZTOT, RTOT
                    READ(NC,*) HUMID, TAIR, TCORN, TTOT
                    READ(NC,*) TMIN,TMAX,TINCR
                    READ(NC,*) ZMIN,ZMAX,ZINCR
                    READ(NC,*) RMIN,RMAX,RINCR
                 IF (NDIST .EQ. 1) THEN
                         READ(NC,*) RJ(1), RJ(2), RJ(3), RJ(4)
                         READ(NC,*) BB(1), BB(2), BB(3), BB(4)
                         READ(NC,*) SL(1), SL(2), SL(3), SL(4)
                 ENDIF
        ELSE
        GO TO 1030
        END IF
C
C       We only get here after reading the complete data field
C             go to calculation, since first time through
        go to 1030
C       Entry point from end of program is at 1020
 1020   IF (NUMID .GT. NTFIN) THEN
C               Done last computation condition under current root name
C               Test if more root names, more in batch, or exit
                if(ncntg .eq. 0 .and. ncntb.ne.0) go to 1000
                if(ncntg .eq. 0 .and. ncntb.eq.0) go to 2000
        ELSE
                go to 1010
        END IF
C
 1030   NTWO = NUMID
        NUMID=NUMID+1

C
C****************************************************************
************************START OF COMPUTATIONS********************
*****************************************************************
C
```

```
C*******************INITIALIZE *******************************
C
C-----CALCULATE NUMBER OF STEPS IN EACH DIRECTION
C
      NR = INT(RTOT/DR+0.3) + 1
      NZ = INT(ZTOT/DZ+0.3) + 1
      NT = INT(TTOT/DT+0.3)
C
C-----INITIALIZE TEMPERATURES AND DAMAGE INTEGRALS
C     TEMPERATURES IN V(I,J) AND VN(I,J) NEED CORRECT STARTING VALUE
C
C-----INITIALIZE DAMAGE PARAMETER TO ZERO
C
      OMEGA1=0.0
      OMEGA2=0.0
C
C
C
      DO 1 I=2,NZ+1
      A(I)=0.0
      PD(I)=0.0
      EVAPX(I)=0.0
        DO 2 J=2,NR+1
           V(I,J)=TCORN
           VN(I,J)=TCORN
           DINT1(I,J)=0.0
           DINT2(I,J)=0.0
    2   CONTINUE
    1 CONTINUE
C
C-----CALCULATE CONSTANTS
C
      C1 = K*DT/(2.0*DR)
      C2 = K*DT/(DZ**2.0)
      C3 = K*DT/(DR**2.0)
C
C
C*************COMPUTE PARAMETERS TO CONTROL DATA WRITES***********
C
C
      LMIN=NINT (TMIN/DT)
      LMAX=NINT (TMAX/DT)
      LINCR=NINT (TINCR/DT)
C    COMPUTE A CONTROL PARAMETER FOR PRINTING CALLED LHIT
C    THE FIRST ENTRY USES LHIT=LMIN, AND IT IS INCREMENTED
      LHIT=LMIN
      IZMIN=NINT (ZMIN/DZ) + 2
      IZMAX=NINT (ZMAX/DZ) + 2
      IZINC=NINT (ZINCR/DZ)
      JRMIN=NINT (RMIN/DR) + 2
      JRMAX=NINT (RMAX/DR) + 2
      JRINC=NINT (RINCR/DR)
C
C*************OPEN OUTPUT FILE FOR BINARY WRITES*****************
C
C-------GET A NAME FOR THIS DATA SET-------
      EXT='BIN'
      CALL NAM6P2 (ROOTNM, NTWO, EXT, NAME)
C
      OPEN(UNIT=NOUT, FILE=NAME, FORM='UNFORMATTED',
     U  RECORDTYPE='FIXED',BLOCKSIZE=32768)
C
```

```
C       NOTE THAT THE BINARY WRITE WILL HAVE A FIXED NUMBER OF VARIABLES
C       PER LINE DEFINED BELOW IN THE COMPUTATION.  WE NEED TO SPECIFY
C       THE SAME NUMBER OF REAL VARIABLES PER LINE (ACTUALLY SAME # BYTES)
C       WE ALSO SHOULD WRITE EXTRA LINES IN CASE FUTURE VERSIONS REQUIRE
C       MORE INPUT DATA TO DEFINE BEAM PARAMETERS OR PULSING OPTIONS
C       THE CHARACTER VARIABLE OF LENGTH N USES N BYTES, INTEGERS USE 4 IN
C       STANDARD FORTRAN.
C
C       IT WOULD BE USEFUL TO WRITE OUT THE DATE AND TIME USING WATCOM
C       ENVIRONMENT SUBROUTINES
C       GETDAT, HAS 3 ARGUMENTS OF TYPE INTEGER*2; 2 BYTES/VARIABLE
C       GETTIM, HAS 4 ARGUMENTS OF TYPE INTEGER*2;
            CALL GETDAT (YEAR,MONTH,DAY)
            CALL GETTIM (HRS,MINS,SECS,HSECS)

C       DEFINE A REAL VARIABLE WITH 0.0 TO USE AS A 4 BYTE FILL
            QX=0.0
C
            WRITE (NOUT) ROOTNM, NTWO, ALPHA, NDIST, PWR, THEAT, TFILL
            WRITE (NOUT) DZ,DR,DT,ZTOT,RTOT,HUMID,TAIR
            WRITE (NOUT) TCORN,TTOT,TMIN,TMAX,TINCR,ZMIN,ZMAX
            WRITE (NOUT) ZINCR,RMIN,RMAX,RINCR,RJ(1),RJ(2),RJ(3)
            WRITE (NOUT) RJ(4),BB(1),BB(2),BB(3),BB(4),SL(1),SL(2)
            WRITE (NOUT) SL(3),SL(4),QX,QX,QX,QX,QX
            WRITE (NOUT) QX,QX,QX,QX,QX,QX,QX
            WRITE (NOUT) QX,QX,QX,QX,QX,QX,QX
            WRITE (NOUT) QX,QX,QX,QX,QX,QX,QX
            WRITE (NOUT) YEAR,MONTH,DAY,HRS,MINS,SECS,HSECS,QX,QX,QX,TFILL
C       TENTH LINE HAS THE DATE AND TIME DATA WITH A FILL OF 14 BYTES
C
C
C
C****************************************************************
C************ START OF MAIN TIME LOOP ****************************
C
C
            DO 5 L=1,NT
            T = L*DT
C
            Q=0.0
C       RESET Q PARAMETER TO COMPUTE EVAPORATION THICKNESS/LOOP
C
C-----CONVECTIVE BOUNDARY AT SURFACE
C
            DO 12 J=3,NR+1
               R=(J-2.0)*DR
               CALL POWER(PD(J),R,ALPHA,PWR,NDIST,THEAT,T,RJ,BB,SL)
               CALL VAPOR(V(2,J),A(J),ALPHA,HUMID,PD(J),Q)
               EVAPX(J)=EVAPX(J) + (Q*DT)
               Z=0.0
               V(1,J)=(V(2,J)+(H/K)*TAIR*DZ)/(1.0+(H/K)*DZ)
               VN(2,J)=V(2,J)+(A(J)*DT)*EXP(-ALPHA*Z)
      U            +(C1/R)*(V(2,J+1)-V(2,J-1))
      U            +C2*(V(3,J)-2.0*V(2,J)+V(1,J))+C3*(V(2,J+1)
      U            -2.0*V(2,J)+V(2,J-1))

12   CONTINUE
C
C-----ZERO DERIVATIVE BOUNDARY CONDITION AT CENTER
C-----OF CYLINDER
C
            R=0.0
```

```
          CALL VAPOR(V(2,2),  2),ALPHA,HUMID,PD(2),Q)
          EVAPX(2)=EVAPX(2) + (Q*DT)
          V(1,2)=(V(2,2)+(H/K)*TAIR*DZ)/(1.0+(H/K)*DZ)
          VN(2,2)=V(2,2)+(A(2)*DT)+
     U       C2*(V(3,2)-2.0*V(2,2)+V(1,2))+2.0*C3*
     U       (V(2,3)-V(2,2))
C
C-----CALCULATE ALL OTHER GRID POINTS
C
          DO 20 I=3,NZ
          Z=(I-2.0)*DZ
            DO 30 J=3,NR
            R=(J-2.0)*DR
            VN(I,J)=V(I,J)+(A(J)*DT)*EXP(-ALPHA*Z)
     U          +(C1/R)*(V(I,J+1)-V(I,J-1))
     U          +C2*(V(I+1,J)-2.0*V(I,J)+V(I-1,J))
     U          +C3*(V(I,J+1)-2.0*V(I,J)+V(I,J-1))
30          CONTINUE
C
C-----ZERO DERIVATIVE B.C. AT CENTER OF CYLINDER
C
          R=0.0
          VN(I,2)=V(I,2)+((A(2)*DT)*EXP(-ALPHA*Z))
     U          +C2*(V(I+1,2)-2.0*V(I,2)
     U          +V(I-1,2))
     U          +2.0*C3*(V(I,3)-V(I,2))
20    CONTINUE
C
C-----DAMAGE INTEGRAL CALCULATION
C
          DO 31 I=2,NZ
            DO 32 J=2,NR
            OMEGA1=EXP(LOG(DT*(VN(I,J)+273.0)*2.081E10)+191.495
     U          -(7.549E04/(VN(I,J)+273.0)))
            DINT1(I,J)=DINT1(I,J)+OMEGA1
            OMEGA2=EXP(LOG(DT*(VN(I,J)+273.0)*2.081E10)+196.276
     U          -(7.700E04/(VN(I,J)+273.0)))
            DINT2(I,J)=DINT2(I,J)+OMEGA2
C     OPTION TO PRINT MAXIMUM VALUE OF 1.0 FOR OMEGA
C           IF (DINT2(I,J) .GE. 1.00) DINT2(I,J)=1.00
C           IF (DINT1(I,J) .GE. 1.00) DINT1(I,J)=1.00
32          CONTINUE
31    CONTINUE
C
C*****************************************************************
C-----WRITE FILE OF TEMPERATURES AND OTHER DATA PERIODICALLY
C*****************************************************************
C
C     THE TIME VARIABLE IS THE PRIMARY SELECTION CRITERIA.
C     THIS IS SET UP, ALONG WITH OTHER PARAMETERS, BEFORE ENTERING
C     THE MAIN LOOP.
C
C     CONVERT INPUT REQUEST INTO PARAMETERS FOR DO LOOPS ON Z & R
C     THE ZMIN AND ZMAX DEFINE THE START AND END Z DIMENSION
C     THE RMIN AND RMAX DEFINE THE START AND END R DIMENSION
C     BOTH INCREMENTS ARE THE COMPUTED DELTAS, DZ AND DR, SO
C     SELECTING INTEGRAL MULTIPLES IS DESIREABLE, HOWEVER, THE CODE
C     PICKS THE NEAREST INTEGER BY NINT FUNCTION.
C
          IF(L .GE. LMIN) THEN
            IF(L .EQ. LHIT) THEN
C     BOTH LOOPS MUST START WITH 2 TO HAVE CORRECT ARRAYS
```

```
                       DO 36
                       DO 5 J=JRMIN, JRMAX, JRINC
                       Z=(I-2.0)*DZ
                       R=(J-2.0)*DR
                       WRITE (NOUT) T,R,Z,VN(I,J),
     U                          DINT1(I,J),DINT2(I,J),EVAPX(J)
C
   36             CONTINUE
   35          CONTINUE
                  LHIT=LHIT+LINCR
                  IF (LHIT .GT. LMAX) THEN
                     LHIT=LHIT-LINCR
                  END IF
               END IF
            END IF
C
C
C-----INCREMENT TEMPERATURES FOR NEXT TIME STEP
C
         DO 40 I=2,NZ
               DO 50 J=2,NR
               V(I,J)=VN(I,J)
   50       CONTINUE
   40 CONTINUE
C
C  RETURN OF MAIN LOOP
C
    5 CONTINUE
C********************* END OF MAIN LOOP *************************
C***************************************************************
C
C**************DECISION IF MORE INPUT DATA SETS, ALSO***********
C     **********BINARY OPENS FILES, SO THEY NEED CLOSING*******
C
         CLOSE (NOUT)
C     NOW DECIDE IF MORE FILES ARE IN THE BATCH
C     Return to 1020 for tests
         GO TO 1020
C
C***************************************************************
C     CLOSE CONNECTION TO CONSOLE INPUT (REDIRECTED TO FILE)
 2000 CLOSE (NC)
C
  100 FORMAT (1X,F4.1,3X,F5.3,3X,F5.3,2X,F7.3,2X,E9.4,2X,E9.4,2X,F9.7)
         STOP
         END
C********************* END OF MAIN PROGRAM**********************
C***************************************************************
C***************************************************************
C
C
C***************************************************************
C***************************************************************
C-----SUBROUTINE TO CALCULATE POWER DENSITY
C-----FROM BEAM PROFILE MEASUREMENT
C
         SUBROUTINE POWER(PD,R,ALPHA,PWR,NDIST,THEAT,T,RJ,BB,SL)
C     FIRST DECIDE IF THE POWER IS STILL ON AT THE GIVEN TIME, T
C     SELECT THE DISTRIBUTION FOR THIS CALCULATION
C
C     THE ONLY PARAMETER DEFINING TIME IS THE PULSE DURATION, TH.
C
         DIMENSION RJ(5), BB(4), SL(4)
```

```
                    PD=0.0
                    GO TO 900
              END IF
C
C     BRANCH TO BLOCK WITH A COMPUTED GO TO BASED ON NDIST
C     ALLOWS ADDITION OF MULTIPLE DISTRIBUTIONS IN ONE PROGRAM
C
              GO TO (100, 200) NDIST
       50 STOP 'STOPPED--ERROR IN SELECTION OF POWER DISTRIBUTION'
C
C     ****************** NDIST=1 *********************************
C     NDIST=1, DISTRIBUTION IS PIECEWISE DEFINED BY STRAIGHT LINES
C     OVER 4 SECTIONS, DATA IN RJ(I) DEFINES THE POINTS OF SEPARATION
C     AND BB(I) IS THE INTERCEPT AND SL(I) THE SLOPE
C
C     FIRST TEST IF RADIUS IS OUTSIDE BEAM LIMIT, ARBITRARY POINT IS THE
C     VALUE IN RJ(1); THE RJ(5) VALUE IS THE INNER POINT OF R=0.0
      100 RJ(5)=0.0
          IF (R .GE. RJ(1)) THEN
                    PD=0.0
                    GO TO 900
          END IF
C     NOW DO SPECIFIC RADIAL RANGES ACCORDING TO LINEAR EQUATIONS
          DO 120 I=1,4
          IF (RJ(I) .EQ. 0.0 ) THEN
               GO TO 900
          ENDIF
          IF (R .LT. RJ(I) .AND. R .GE. RJ(I+1)) THEN
               PD=(BB(I) + SL(I)*R)*PWR*45.095*ALPHA
          ENDIF
      120 CONTINUE
          GO TO 900
C
C     ***********************************************************
C     EXPANSION LIST OF OPTIONS
C     MAKE NDIST=2 CORRESPOND TO A DISK OF MAXIMUM SIZE
C
      200 GO TO 50
      900 CONTINUE
          RETURN
          END
C
C***************************************************************
C***************************************************************
C-----SUBROUTINE TO CALCULATE POWER DENSITY LOSS DUE TO
C-----EVAPORATIVE COOLING
C
C     IF VAPOR COOLING IS TO BE OMMITTED THEN THE CALLS TO THIS ROUTINE
C     SHOULD BE COMMENTED AND A NEW LINE A(J) = PD(J) ADDED BELOW THE
C     COMMENTED LINE
C
C
          SUBROUTINE VAPOR(TEMP,A,ALPHA,HUMID,PD,Q)
          P = 83.71*EXP(-5.164E03*((1.0/(TEMP+273.))-0.00312))
          H = 0.622*(P/(760.-P))
          DA = 1.6513*ALPHA*(H-HUMID)
          Q=0.002897*(H-HUMID)
          A = PD-DA
          RETURN
          END
C
C     OPTIONAL TO INCLUDE BEFORE END STATEMENT
```

```
C           SUM = 0.0
C           DO 60 I=2,NZ
C           DO 70 J=2,NR
C           CALS = DR*DZ*(V(I,J)-37.3)
C           SUM = SUM + CALS
C    70 CONTINUE
C    60 CONTINUE
C           WRITE (*,*) SUM
C***************************************************************
C***************************************************************
C*****************NAM6P2****************************
C
C      SUBROUTINE TO CONVERT A 6 CHARACTER (OR LESS) NAME, A TWO
C      DIGIT INTEGER VALUE AND A THREE CHARACTER EXTENSION INTO A
C      LEGITIMATE 8 CHAR DOS FILE NAME HAVING A THREE CHAR EXTENSION
C
C      NEEDS CONVERSIONS OF TWO DIGIT INTEGERS INTO ASCII******
C      *******CALLS SUBROUTINE TWOCHR(NTWO,ASCNUM)**********
C
C      THE PROBLEM OF EXTRA BLANKS IN A NAME IS BAD FOR USING NAMES
C      IN DOS FILES.  FORTRAN IS A PAIN WITH CHARACTERS.
C      THEREFORE WE WILL PAD THE NAME WITH 'X' AS NEEDED
C
       SUBROUTINE NAM6P2 (NBASE,NTWO,EXT,NAME)
       CHARACTER NBASE*6,EXT*3,NAME*12,ASCNUM*2
C
C      NBASE IS 6 CHAR NAME THAT MAY BE DEFINED WITH <6, GIVING BLANKS
C      NTWO IS THE TWO DIGIT INTEGER THAT NEEDS TO BE ASCII
C      EXT IS A 3 CHAR NAME FOR THE EXTENSION
C      NAME IS THE RETURNED NAME, EG, NAMFIL45.ASC, WITH NTWO=45.
C      THE ERROR OF <2 OR >2 DIGIT INTEGER IS HANDLED BELOW BY
C      FILL OR TRUNCATION.
C
C      FIRST TEST IF ANY BLANKS IN NBASE
       J=INDEX(NBASE,' ')
       IF( J .EQ.0) THEN
              GO TO 100

END IF
C      NOW WE NEED TO FILL IN CHARACTERS TO MAKE A TOTAL OF SIX
       DO 20 I=J,6
       NBASE(I:I)='X'
    20 CONTINUE
C
C      NOW WE CAN CREATE A FULL NAME
C      FIRST NEED TO CONVERT A TWO DIGIT INTEGER TO AN ASCII VALUE.
C      WILL TEST IF A ONE DIGIT AND A THREE DIGIT INTEGER AND EITHER
C      ADD 10 OR TRUNCATE TO THE LAST TWO DIGITS.  MORE THAN 3 IS BAD
   100 ATWO=REAL(NTWO)
C      FIRST TEST IF MORE THAN THREE DIGITS, IF SO MAKE UP 'YY'
       IF (ATWO .GT. 999.) THEN
              ASCNUM='YY'
C      NEED TO BYPASS CALL TO SUBROUTINE
              GOTO 300
       END IF

A1=MOD(ATWO,10.)
       A2=MOD(ATWO,100.)
       IF (ATWO .LT. 10.) THEN
              ATWO=ATWO+10.
              GO TO 200
C---ADD 10 TO SINGLE DIGIT AND GO ON TO END
```

```
          IF (ATWO .  .99. .AND. ATWO .GE. 10..    THEN
          GO TO 200
C----THIS IS A TWO DIGIT NUMBER, GO ON TO END
          ELSE
                    ATWO=A2
C---THIS SEQUENCE EXTRACTS LAST TWO DIGITS OF THREE DIGIT NUMBER
          END IF
       END IF
C
  200 CONTINUE
C       NOW CALL THE SUBROUTINE TO CONVERT TWO DIGIT INTEGER TO ASCII
          N=INT(ATWO)
          CALL TWOCHR(N,ASCNUM)
C       CONCATENATE AND END THE SUBROUTINE WITH OUTPUT NAME
  300 NAME=NBASE//ASCNUM//'.'//EXT
          END
C
C***************************************************************
C****************** TWOCHR ************SUBR***************
C       CONVERSION OF A TWO DIGIT INTEGER NUMBER INTO AN ASCII
C       TWO DIGIT VALUE THAT CAN BE USED FOR A FILE NAME
C
          SUBROUTINE TWOCHR(NTWO,ASCNUM)
          CHARACTER ASCNUM*2, A*1,B*1
C
C       ASSUME THAT NTWO IS A TWO DIGIT INTEGER NUMBER
C       FIRST DO THE TENS PLACE BY FINDING THE NUMBER
          TWO=REAL(NTWO)
          X=AINT (TWO/10.)
C       CONVERT TO AN ASCII CODE BY ADDING 48, WHERE 48='0'
          J=INT(X)+48
          A=CHAR(J)
C       NOW DO THE DIGIT PLACE
          Y=MOD(TWO,10.)
          J=INT(Y)+48
          B=CHAR(J)
C       NOW ASSEMBLE THE TWO PIECES
          ASCNUM=A//B
          END
```

What is claimed is:

1. A method for changing the shape of a cornea having a central optical axis, comprising the steps of: positioning a laser to irradiate said cornea; and irradiating said cornea with a laser beam from said laser, said laser beam having a power density profile in a treatment pattern, said laser beam having a wavelength such that the absorption coefficient of said wavelength in water ranges from 5 cm$^{-1}$ to 114 cm$^{-1}$, with an energy sufficient to and for a time sufficient to necrotize stromal keratocytes in a selected treatment volume without substantially shrinking collagen in said cornea, said treatment depth having a posterior boundary of at least 50% of the stromal depth.

2. The method of claim 1 wherein said selected treatment volume has a posterior boundary equal to the total stromal depth in said cornea.

3. The method of claim 1 wherein said selected treatment volume has a posterior boundary equal to from about 50% to 90% of the stromal depth in said cornea.

4. The method of claim 1 wherein said time is between about 1.5 to 15 seconds.

5. The method as recited in claim 1 including the step of directing said laser beam onto the cornea in multiple treatments over short time intervals between about 10 seconds and 1 hour.

6. The method as recited in claim 1 including the step of directing said laser beam onto the cornea continuously.

7. The method as recited in claim 1 including the step of directing said laser beam onto the cornea with modulation.

8. The method of claim 1 wherein the step of irradiating comprises irradiating with a laser beam having a center and a periphery such that the power density profile of said laser beam is higher near the periphery of said treatment pattern than near the center thereof.

9. The method of claim 1 wherein the irradiating step comprises irradiating with a laser beam having a power density profile which varies across said treatment pattern to create an approximately equal temperature profile across said treatment pattern at any given depth of said treatment volume during application of laser energy.

10. The method of claim 1 wherein the step of irradiating includes generating said treatment pattern as a substantially circular treatment region, having a diameter of between about 2 mm to 12 mm and centered on said central optical axis of said cornea.

11. The method of claim 1 wherein the step of irradiating includes generating said treatment pattern as a plurality of symmetrical, spaced apart, radial treatment sectors having a radial length of from about 1 mm to 6 mm, said radial sectors disposed about an untreated subtantially circular central region having a radius of between about zero to 4 mm, said radial sectors separated by untreated radial regions and centered on said central optical axis of said cornea.

12. The method of claim 1 wherein the step of irradiating includes generating said treatment pattern centered on said central optical axis of said cornea as a plurality of symmetrical, spaced apart, radial treatment sectors having a radial length of from about 1 mm to 6 mm disposed about a central substantially circular treatment region having a diameter of between about zero to 3 mm said radial treatment sectors separated from said circular treatment region by an untreated annular region having a radial width of from about 0.25 to 2 mm.

13. The method of claim 1 wherein the step of irradiating includes generating said treatment pattern centered on said central optical axis of said cornea as a plurality of concentric treatment annuli disposed about a substantially circular central treatment region having a radius of from about zero to 3 mm, a first treatment annuli having a radial width of from about 0.25 to 2 mm and separated from said central treatment region by a first untreated annular region having a radial width of from about 0.25 to 2 mm, a second treatment annuli having a radial width of from about 0.25 to 2 mm and separated from said first annuli by a second untreated region having a radial width of from about 0.25 to 2 mm.

14. The method of claim 1 wherein the step of irradiating in said treatment pattern includes irradiating a pair of radial treatment sectors located symmetrically on opposite sides of said central optical axis of said cornea, said radial treatment sectors having a radial length of from about 0.25 mm to 6 mm disposed about a central untreated region comprising a substantially circular region centered on said central optical axis and having a radius of from about zero to 6 mm.

15. The method of claim 1 wherein the step of irradiating in said treatment pattern includes irradiating a pair of substantially circular treatment zones located symmetrically on opposite sides of said central optical axis of said cornea, said circular treatment zones having diameters of from about 0.25 to 4 mm and whose centers lie on a circle having a radius of from about zero to 6 mm.

16. The method as recited in claim 1 in which the step of irradiating includes pumping a laser medium by a diode laser.

17. The method as recited in claim 1 including generating the laser beam with means including a laser medium containing $Co^{+2}$ ions in an $M_gF_2$ crystalline media.

18. The method as recited in claim 17 in which the step of irradiating includes pumping a laser medium by a diode laser.

19. The method of claim 1 including generating the laser beam from a diode laser.

20. The method as recited in claim 1 including generating the laser beam with means including a crystalline laser medium containing ions selected from the group consisting of $Holmium^{+3}$ ions, $Thulium^{+3}$ ions, $Erbium^{+3}$ ions and mixtures thereof.

21. The method as recited in claim 20 in which the step of irradiating includes pumping a laser medium by a diode laser.

22. The method of claim 1 wherein the step of irradiating includes generating said treatment pattern centered on said central optical axis of said cornea as a first treatment annulus concentrically disposed about a substantially circular central untreated region having a radius of from about zero to 4 mm, said first treatment annulus having a radial width of from about 0.5 to 3 mm.

23. The method of claim 22 wherein generating said treatment pattern further includes generating a second treatment annulus concentrically disposed about said first treatment annulus, said second treatment annulus having a radial width of from about 0.5 to 2 mm and separated from said first annuli by an untreated annular region having a radial width of from about 0.25 to 2 mm.

* * * * *